United States Patent
Johnson et al.

(10) Patent No.: US 9,603,329 B2
(45) Date of Patent: Mar. 28, 2017

(54) WHEAT CULTIVAR 'GA 04570-10E46'

(71) Applicant: University of Georgia Research Foundation, Inc., Athens, GA (US)

(72) Inventors: Jerry W. Johnson, Griffin, GA (US); G. David Buntin, Griffin, GA (US); James W. Buck, Fayetteville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 14/970,039

(22) Filed: Dec. 15, 2015

(65) Prior Publication Data

US 2016/0183490 A1    Jun. 30, 2016

Related U.S. Application Data

(60) Provisional application No. 62/096,731, filed on Dec. 24, 2014.

(51) Int. Cl.
*A01H 5/10* (2006.01)

(52) U.S. Cl.
CPC ..................... *A01H 5/10* (2013.01)

(58) Field of Classification Search
None
See application file for complete search history.

(56) References Cited

U.S. PATENT DOCUMENTS 8,766,063 B1 *   7/2014   Clarkson .................. A01H 5/10
                                                        426/622

* cited by examiner

*Primary Examiner* — Cynthia Collins
(74) *Attorney, Agent, or Firm* — Klarquist Sparkman, LLP

(57) ABSTRACT

Herein provided is a new wheat cultivar designated 'GA 04570-10E46' as well as the seeds, plants and derivatives of the new wheat variety 'GA 04570-10E46' (such as cultivars and hybrids related thereto). Also provided are tissue cultures of the new wheat variety 'GA 04570-10E46' and the plants regenerated therefrom. Methods for producing wheat plants by crossing the new wheat variety 'GA 04570-10E46' with itself or another wheat variety and plants produced by such methods are also provided.

34 Claims, No Drawings

WHEAT CULTIVAR 'GA 04570-10E46'

CROSS-REFERENCE TO RELATED APPLICATION

This application claims priority to U.S. Provisional Application No. 62/096,731 filed Dec. 24, 2014, herein incorporated by reference.

FIELD

This disclosure provides a new and distinctive wheat cultivar, 'GA 04570-10E46'.

BACKGROUND

Six main wheat market classes exist, five of which belong to the species Triticum aestivum L.: common wheat, hard red winter, hard red spring, soft red winter, and white. The sixth class of wheat is durum (Triticum turgidum L.). Common wheats are used in a variety of food products such as bread, cookies, cakes, crackers, and noodles. In general, the hard wheat classes are milled into flour used for breads and the soft wheat classes are milled into flour used for pastries and crackers. Wheat starch is used in the food and paper industries, as laundry starches, and in other products. Products produced from wheat may include grain, flour, baked goods, cereals, pasta, beverages, livestock feed, biofuel, straw, construction materials, and starches.

Wheat, including soft red winter wheat (Triticum aestivum L.), is an important and valuable field crop. A continual need exists for medium maturing varieties that have a high yield potential with good disease and insect resistance, for example varieties with the maturity and disease and insect resistance necessary in a desired geographical region, such as in the Southeastern United States.

SUMMARY

The present disclosure relates to a new wheat cultivar, 'GA 04570-10E46'. 'GA 04570-10E46' is a soft red winter wheat (Triticum aestivum L.), awned, and white chaffed. It is most similar to the soft red winter wheat 'USG 3120' (unpatented). It can be distinguished by at least the following characteristics: 'GA 04570-10E46' has a sbml gene for resistance to wheat soil-borne Mosaic Virus while 'USG 3120' does not have the sbml gene, and 'GA04570-10E46' also has the Lr37Yr17 gene for resistance to leaf rust while 'USG 3120' does not.

'GA 04570-10E46' is a medium maturing, high yielding, excellent test weight, awned wheat with resistance to current races of leaf rust, Puccinia recondita (Roberge ex Desmaz), and stripe rust, Puccinia striiform is Westend, and is resistant in the field to biotypes of Hessian flies, (Mayetiola destructor (Say)) in Georgia. 'GA 04570-10E46' is resistant to stem rust races, QFCSC, QTHJC, RCRSC, RKQQC, TTTTF, SCCSC, and QCCSM and is resistant to leaf rust races, MCTNB, TDBGG, TBBGJ, TNRJ, MCDS, KFBJ, MLDS, TCRKG, TFBJ, and TCTSB. It is also resistant to wheat soil-borne mosaic virus and has good powdery mildew resistance. Milling and baking quality characteristics of 'GA 04570-10E46' are rated as acceptable for soft red winter wheat use. Thus, the new variety is adapted to areas of the United States (such as the southern and southeastern United States, for example areas south of Albany, Ga.), such as areas that are known to have or expected to have damaging levels of leaf rust, stem rust, stripe rust, soil-borne mosaic virus, powdery mildew and/or Hessian flies.

'GA 04570-10E46' exceeded the grain yield of 'AGS 2035' and 'Baldwin'. 'G06-3183RR' thus could be used as a replacement for 'AGS 2035' and 'Baldwin'.

A deposit of the new wheat variety 'GA 04570-10E46' was made with the American Type Culture Collection (ATCC), 10801 University Blvd., Manassas, Va., 20110. The date of deposit is Dec. 1, 2016. The deposit is intended to meet all of the requirements of 37 C.F.R. §§1.801-1.809. The accession number for those deposited seeds of the new wheat cultivar 'GA 04570-10E46' is ATCC Accession No. PTA-123659. The deposit will be maintained in the depository for a period of 30 years, or 5 years after the last request, or for the effective life of the patent, whichever is longer, and will be replaced if necessary during that period. In one embodiment, the disclosure provides wheat seed deposited as ATCC Accession No. PTA-123659, as well as bulk wheat seed containing such seeds.

The disclosure provides wheat plants having or consisting of the morphological and physiological characteristics of 'GA 04570-10E46', such as the characteristics noted in Tables 1-15, for example medium maturing, high yield, excellent test weight, resistance to leaf rust (e.g., races MCTNB, TDBGG, TBBGJ, TNRJ, MCDS, KFBJ, MLDS, TCRKG, TFBJ, and TCTSB), stem rust (e.g., stem rust races, QFCSC, QTHJC, RCRSC, RKQQC, TTTTF, SCCSC, and QCCSM), stripe rust, soil-borne mosaic virus, powdery mildew and/or Hessian flies, and acceptable milling and baking quality characteristics.

Also provided are seeds of such plants, progeny of such plants, parts of such plants (such as pollen, an ovule, a head, an awn, a leaf, an embryo, a cotyledon, a hypocotyl, a meristematic cell, a root, a root tip, a pistil, an anther, a floret, a pericarp, a spike, a stern, a callus, and cells), as well as a tissue culture of wheat cultivar 'GA 04570-10E46'. In one example, the disclosure provides wheat plants having the genotype of 'GA 04570-10E46'. For example, the disclosure provides plants produced by growing the seed of the new wheat cultivar 'GA 04570-10E46'.

The disclosure provides a tissue culture of regenerable cells of the new wheat cultivar 'GA 04570-10E46', as well as plants regenerated therefrom. Such regenerated wheat plants can include or consist of the physiological and morphological characteristics of a plant grown from the seed of the new wheat cultivar 'GA 04570-10E46'. Exemplary regenerable cells include but are not limited to those from protoplasts or cells, such as those from embryos, meristematic cells, ovule, pollen, leaves, roots, root tips, anther, pistil, flower, seed, cotyledon, hypocotyl, shoot, stein, pod, petiole or stem of the new wheat cultivar 'GA 04570-10E46'.

The disclosure also provides a method for producing a wheat seed by a method that includes crossing two wheat plants and harvesting the resultant wheat seed, wherein at least one of the two wheat plants is from the 'GA 04570-10E46' line. The disclosure also provides methods of producing plants and plants that are herbicide tolerant, pest or insect resistant, disease resistant, or have modified fatty acid or carbohydrate metabolisms.

Methods of producing wheat seed from the 'GA 04570-10E46' wheat plants are provided. In some examples such methods include crossing 'GA 04570-10E46' with itself or a second wheat plant and harvesting a resulting wheat seed. In some examples, the second wheat plant has one or more desirable traits, which is/are introduced into plants and seeds resulting from such a cross. For example, the second plant can be transgenic, wherein the transgene confers the desirable trait(s). Seeds produced by such methods, including $F_1$ hybrid seeds, as well as wheat plants or parts thereof produced by growing such a seed, are provided. In some examples, the method of crossing includes planting seeds of the new wheat cultivar 'GA 04570-10E46', cultivating wheat plants resulting from the seeds until the plants bear flowers, allowing fertilization of the flowers of the plants; and harvesting seeds produced from the plants.

Methods are provided for producing a plant of wheat cultivar 'GA 04570-10E46' that has one or more added desired traits, as well as plants and seeds generated from such methods. In one example, such a method provides a wheat plant having a single locus conversion of the new wheat cultivar 'GA 04570-10E46', wherein the wheat plant includes or expresses the physiological and morphological characteristics of the new wheat cultivar 'GA 04570-10E46' (such as those shown in Tables 1-15). In some embodiments, the single locus conversion can include a dominant or recessive allele. Such methods can include introducing a transgene that confers one or more desired traits into a plant of the new wheat cultivar 'GA 04570-10E46'. Exemplary desired traits include herbicide tolerance, resistance to an insect, resistance to a bacterial disease, resistance to a viral disease, resistance to a fungal disease, resistance to a nematode, resistance to a pest, male sterility, site-specific recombination; abiotic stress tolerance (such as tolerance to drought, heat, cold, low or high soil pH level, and/or salt); modified phosphorus characteristics, modified antioxidant characteristics, modified essential seed amino acid characteristics, modified fatty acid metabolism, modified carbohydrate metabolism, decreased phytate, or other improved nutritional qualities.

Methods of introducing a single locus conversion (such as a desired trait) into the new wheat cultivar 'GA 04570-10E46' are provided. In some examples the methods include (a) crossing a plant of cultivar 'GA 04570-10E46' with a second plant having one or more desired traits to produce $F_1$ progeny plants; (b) selecting $F_1$ progeny plants that have the desired trait to produce selected $F_1$ progeny plants; (c) crossing the selected progeny plants with at least a first plant of cultivar 'GA 04570-10E46' to produce backcross progeny plants; (d) selecting backcross progeny plants that have the desired trait and physiological and morphological characteristics of wheat cultivar 'GA 04570-10E46' to produce selected backcross progeny plants; and (e) repeating steps (c) and (d) one or more times in succession to produce selected second or higher backcross progeny plants that comprise the desired trait and the physiological and morphological characteristics of wheat cultivar 'GA 04570-10E46' when grown in the same environmental conditions. In some embodiments, the single locus confers a desirable trait, such as herbicide tolerance, resistance to an insect, resistance to a bacterial disease, resistance to a viral disease, resistance to a fungal disease, resistance to a nematode, resistance to a pest, male sterility, site-specific recombination; abiotic stress tolerance (such as tolerance to drought, heat, low or high soil pH level, and/or salt), modified phosphorus characteristics, modified antioxidant characteristics, modified essential seed amino acid characteristics, decreased phytate, modified fatty acid metabolism, and modified carbohydrate metabolism. In some examples, the single locus confers the ability to synthesize a protein encoded by a gene located within the single locus.

Methods of producing a wheat plant derived from the new wheat cultivar 'GA 04570-10E46', such as an inbred wheat plant, are provided. In particular examples the method includes (a) preparing a progeny plant derived from the new wheat cultivar 'GA 04570-10E46' by crossing a plant of 'GA 04570-10E46' with a wheat plant of a second variety; and (b) crossing the progeny plant with itself or a second plant to produce a progeny plant of a subsequent generation which is derived from a plant of the new wheat variety 'GA 04570-10E46'. In some embodiments, the method further includes (c) growing a progeny plant of a subsequent generation from said seed and crossing the progeny plant of a subsequent generation with itself or a second plant; and (d) repeating steps (b) and (c) for at least 2 additional generations (such as at least 3, at least 5, or at least 10 additional generations, such as 2, 3, 4, 5, 6, 7, 8, 9, 10, 11, 12, 13, 14, 15, 16, 17, 18, 19 or 20 additional generations) with sufficient inbreeding to produce an inbred wheat plant derived from the new wheat cultivar 'GA 04570-10E46'. In other examples, the method includes (a) crossing a wheat plant derived from the new wheat cultivar 'GA 04570-10E46' with itself or another wheat plant to yield additional wheat cultivar 'GA 04570-10E46'-derived progeny wheat seed; (b) growing the progeny wheat seed of (a) under plant growth conditions, to yield additional wheat cultivar 'GA 04570-10E46'-derived wheat plants; and (c) repeating the crossing and growing steps of (a) and (b) from 0 to 7 times (such as 0 to 4 or 1 to 5 times, such as 0, 1, 2, 3, 4, 5, 6, or 7 times) to generate further wheat cultivar 'GA 04570-10E46'-derived wheat plants.

Methods are provided for developing a new wheat plant using the new 'GA 04570-10E46' variety. For example, the methods can include using 'GA 04570-10E46' plants or parts thereof as a source of breeding material in plant breeding techniques, such as recurrent selection, mass selection, bulk selection, backcrossing, pedigree breeding, genetic marker-assisted selection and genetic transformation. In some examples, a plant of the new wheat cultivar 'GA 04570-10E46' is used as the male or female parent.

The disclosure provides a first generation ($F_1$) hybrid wheat seed produced by crossing a plant of the new wheat cultivar 'GA 04570-10E46' to a second wheat plant. In some embodiments, the $F_1$ hybrid wheat plant is grown from the hybrid seed produced by crossing the new wheat variety 'GA 04570-10E46' to a second wheat plant. In specific examples, provided is a seed of an $F_1$ hybrid plant produced with the new wheat variety 'GA 04570-10E46' as one parent, the second generation ($F_2$) hybrid wheat plant grown from the seed of the $F_1$ hybrid plant, and the seeds of the $F_2$ hybrid plant.

Methods of producing hybrid wheat seeds are also provided. In one example the method includes crossing the new wheat cultivar 'GA 04570-10E46' to a second, distinct wheat plant which is nonisogenic to the new wheat variety 'GA 04570-10E46'. In some examples, the method includes cultivating wheat plants grown from seeds of the new wheat variety 'GA 04570-10E46' and cultivating wheat plants grown from seeds of a second, distinct wheat plant, until the plants bear flowers. A flower on one of the two plants is cross pollinated with the pollen of the other plant, and the seeds resulting from such a cross are harvested.

The disclosure also provides wheat plants and parts thereof produced by any of the methods disclosed herein. Thus, provided herein are plants of wheat cultivar 'GA 04570-10E46' that further include a single locus conversion, such as one or more desired traits, for example produced by backcrossing or genetic transformation. In some embodiments, the wheat plants produced by the disclosed methods includes at least two, at least three, at least four, at least five, or at least 10 of the traits of the new wheat variety 'GA '04570-10E46' as described herein. In some embodiments, the wheat plants produced by the disclosed methods include at least two, at least three, at least four, at least five, or at least 10 of the traits of the new wheat cultivar 'GA 04570-10E46' (see Tables 1-15), such as 2, 3, 4, 5, 6, 7, 8, 9 or all 10 of medium maturing, high yield, excellent test weight, resistance to leaf rust (e.g., races MCTNB, TDBGG, TBBGJ, TNRJ, MCDS, KFBJ, MLDS, TCRKG, TFBJ, and TCTSB), resistance to stem rust (e.g., stem rust races, QFCSC, QTHJC, RCRSC, RKQQC, TTTTF, SCCSC, and QCCSM), resistance to stripe rust, resistance to soil-borne mosaic virus, resistance to powdery mildew, resistance to Hessian flies, and acceptable milling and baking quality characteristics, as described herein.

Compositions that include a seed or plant part of wheat cultivar 'GA 04570-10E46' and a cultivation medium (such as a plant seed growth media), are provided. In some examples, the cultivation medium is soil or a synthetic medium. Such media can provide adequate physical support for seeds or other plant parts and can retain moisture and/or nutritional components. Any plant seed growth media may be utilized, and may include polymers or hydrogels. In specific embodiments, the growth medium is present in a container or may, for example, be soil in a field.

Methods of producing a commodity plant product are provided. In some examples the method includes obtaining or supplying a plant of the new wheat cultivar 'GA 04570-10E46', or a part thereof, and producing the commodity plant product therefrom. In some examples the method includes growing and harvesting the plant, or a part thereof. Exemplary commodity plant products include but are not limited to grain, flour, biofuel, straw, and starch. Also provided are products that include a wheat plant or the part thereof of wheat cultivar 'GA 04570-10E46', wherein the product is grain, flour, a baked good, cereal, pasta, a beverage, livestock feed, biofuel, straw, construction material, bread, cookie, cake, cracker, noodle, or laundry starch. Thus, wheat cultivar 'GA 04570-10E46' is useful for the production of grain, but it can also be used for production of silage harvested in the soft dough stage.

The foregoing and other objects and features of the disclosure will become more apparent from the following detailed description.

DETAILED DESCRIPTION

Description of Terms

The following explanations of terms and methods are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. For example, reference to "comprising a plant" includes one or a plurality of such plants. The term "or" refers to a single element of stated alternative elements or a combination of two or more elements, unless the context clearly indicates otherwise. For example, the phrase "A or B" refers to A, B, or a combination of both A and B. Furthermore, the various elements, features and steps discussed herein, as well as other known equivalents for each such element, feature or step, can be mixed and matched by one of ordinary skill in this art to perform methods in accordance with principles described herein. Among the various elements, features, and steps some will be specifically included and others specifically excluded in particular examples.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. All references cited herein are incorporated by reference.

In some examples, the numbers expressing quantities of ingredients, properties such as molecular weight, reaction conditions, and so forth, used to describe and claim certain embodiments are to be understood as being modified in some instances by the term "about" or "approximately." For example, "about" or "approximately" can indicate +/−20% variation of the value it describes. Accordingly, in some embodiments, the numerical parameters set forth herein are approximations that can vary depending upon the desired properties sought to be obtained by a particular embodiment. Notwithstanding that the numerical ranges and parameters setting forth the broad scope of some examples are approximations, the numerical values set forth in the specific examples are reported as precisely as practicable. The recitation of ranges of values herein is merely intended to serve as a shorthand method of referring individually to each separate value falling within the range.

Awn. The elongated needle-like appendages on the flower- and seed-bearing head at the top of the cereal grain plant (e.g., wheat, common wheat, rye). Awns are attached to the lemmas. Lemmas enclose the stamen and the stigma as part of the florets. Florets are grouped in spikelets, which in turn together comprise the head.

Backcross: The mating of a hybrid progeny back to one of its parents. For example hybrid progeny, for example a first generation hybrid ($F_1$), can be crossed back one or more times to one of its parents. Backcrossing can be used to introduce one or more single locus conversions (such as one or more desirable traits) from one genetic background into another.

Cell: Cell as used herein includes a plant cell, whether isolated, in tissue culture or incorporated in a plant or plant part.

Cross: Synonymous with hybridize or crossbreed. Includes the mating of genetically different individual plants, such as the mating of two parent plants.

Cross-pollination: Fertilization by the union of two gametes from different plants.

Disease Resistance: The ability of a plant to restrict the activities of a specified disease, such as a fungus, virus, or bacterium.

Disease Tolerance: The ability of a plant to endure a specified disease (such as a fungus, virus or bacterium) or an adverse environmental condition and still perform and produce in spite of this disorder.

Essentially all of the physiological and morphological characteristics: Refers to a plant having essentially all of the physiological and morphological characteristics of the referenced plant or cultivar, as determined at a 5% significance level for quantitative data.

$F_1$ hybrid: The first generation progeny of the cross of two nonisogenic plants.

Gene Silencing. A general term describing epigenetic processes of gene regulation, including any technique or mechanism in which the expression of a gene is prevented, for example at the level of transcription or translation.

Genotype: The genetic constitution of a cell, an organism, or an individual (i.e., the specific allele makeup of the individual) usually with reference to a specific character under consideration.

Herbicide Resistance: The ability of a plant to survive and reproduce following exposure to a dose of herbicide that would normally be lethal to the plant.

Herbicide Tolerance: The ability of a plant to survive and reproduce after herbicide treatment.

Hessian fly: *Mayetiola destructor*, is a species of fly that is a significant pest of cereal crops including wheat, barley and rye.

Insect Resistance: The ability of a plant to restrict the activities of a specified insect or pest.

Insect Tolerance: The ability of a plant to endure a specified insect or pest and still perform and produce in spite of this disorder.

Leaf Rust: A disease of wheat characterized by pustules that are circular or slightly elliptical, that usually do not coalesce, and contain masses of orange to orange-brown spores. The disease is caused by the fungus *Puccinia recondite* f. sp. *tritici*. Infection sites primarily are found on the upper surfaces of leaves and leaf sheaths, and occasionally on the neck and awns. Resistance to this disease is scored on scales that reflect the observed extent of the disease on the leaves of the plant. Rating scales may differ (in one example it is a scale of 0 to 9) but in general a low number indicates resistance and higher number suggests different levels of susceptibility.

Lodging: The visual rating of the uprightness of the plants. The score is based on the average of the plants in a plot with a score of 0 to 9, with a score of 0 indicating all plants are erect, and a score of 9 where over about 80% of the plants in a plot are prostrate.

Maturity: The stage of plant growth at which the development of the kernels is complete.

Plant: Includes reference to an immature or mature whole plant, including a plant from which seed, grain, anthers, roots or leaves have been removed. Seed or embryo that will produce the plant is also considered to be the plant.

Plant height. Plant height is taken from the top of the soil to the tip of the plant (excluding awns), and is typically measured in centimeters or inches.

Plant parts. Includes protoplasts, leaves, stems, roots, root tips, anthers, pistils, seed, grain, pericarp, embryo, pollen, ovules, cotyledon, hypocotyl, flower, shoot, tissue, petiole, cells, calli, pods, awn, lemma, floret, spike, meristematic cells, protoplasts, and the like. Includes plant cells of a tissue culture from which wheat plants can be regenerated.

Powdery Mildew: A disease of wheat characterized by white to pale gray, fuzzy or powdery colonies of mycelia, and conidia on the upper surfaces of leaves and leaf sheaths (especially on lower leaves), and sometimes on the spikes. The disease is caused by the fungus *Erysiphe graminis* f. sp. *tritici*. Older fungal tissue is yellowish gray. This superficial fungal material can be rubbed off easily with the fingers. Host tissue beneath the fungal material becomes chlorotic or necrotic and, with severe infections, the leaves may die. Eventually, black spherical fruiting structures may develop in the mycelia, and can be seen without magnification. Resistance to this disease is scored on scales that reflect the observed extent of the disease on the leaves of the plant. Rating scales may differ (in one example it is a scale of 0 to 9) but in general a low number indicates resistance and higher number suggests different levels of susceptibility.

Progeny. Offspring; descendants. Includes an $F_1$ wheat plant produced from the cross of two wheat plants where at least one plant includes wheat cultivar 'GA 04570-10E46. Progeny further includes but is not limited to subsequent $F_2$, $F_3$, $F_4$, $F_5$, $F_6$, $F_7$, $F_8$, $F_9$ and $F_{10}$ generational crosses with the recurrent parental line.

Regeneration. The development of a plant from tissue culture. The cells may, or may, not have been genetically modified. Plant tissue culture relies on the fact that all plant cells have the ability to generate a whole plant (totipotency). Single cells (protoplasts), pieces of leaves, or roots can often be used to generate a new plant on culture media given the required nutrients and plant hormones.

Seed. The part of a flowering plant that typically contains the embryo with its protective coat and stored food and that can develop into a new plant under the proper conditions; fertilized and mature ovule.

Seed yield: The yield in bushels/acre (bu/a) and is the actual yield of the grain at harvest.

Self-pollination: The transfer of pollen from the anther to the stigma of the same plant.

*Septoria* Leaf Blotch or Speckled Leaf Blotch. A disease of wheat, common wheat and durum wheat characterized by irregularly shaped blotches that are at first yellow and then turn reddish brown with grayish brown dry centers, caused by the rust fungus *Septoria tritici*. Resistance to this disease is scored on scales that reflect the observed extent of the disease on the leaves of the plant. Rating scales may differ but in general a low number indicates resistance and higher number suggests different levels of susceptibility.

Single locus converted (conversion) plant: Plants developed by backcrossing, mutation, and/or by genetic transformation, wherein essentially all of the desired morphological and physiological characteristics of a wheat variety are recovered in addition to the characteristics of the single locus transferred into the variety via the backcrossing technique.

Soil Born Mosaic Virus. A disease of wheat characterized by mild green to yellow mosaic, yellow-green mottling, dashes, and parallel streaks, most clearly visible on the youngest leaf. Reddish streaking and necrosis at leaf tips sometimes occurs. Stunting can be moderate to severe, depending on the variety. The disease is caused by a virus which is transmitted by a soilborne fungus-like organism, *Polymyxa graminis*, which makes swimming spores that infect the roots of wheat. Resistance to this disease is scored on scales that reflect the observed extent of the disease on the young plants. Rating scales may differ (in one example it is a scale of 0 to 9) but in general a low number indicates resistance and higher number suggests different levels of susceptibility.

Stem Rust: A disease of wheat characterized by pustules containing masses of spores that are dark reddish brown, and may occur on both sides of the leaves, on the stems, and on the spikes. The disease is caused by the fungus *Puccinia graminis* f. sp. *Tritici*. Resistance to this disease is scored on scales that reflect the observed extent of the disease on the leaves of the plant. Rating scales may differ but in general a low number indicates resistance and higher number suggests different levels of susceptibility.

Stripe Rust: A disease of wheat, common wheat, and durum wheat, and barley characterized by elongated rows of yellow spores on the affected parts, caused by a rust fungus, *Puccinia striiformis*. Resistance to this disease is scored on scales that reflect the observed extent of the disease on the leaves of the plant. Rating scales may differ (in one example it is a scale of 0 to 9) but in general a low number indicates resistance and higher number suggests different levels of susceptibility.

Test Weight. A measure of density that refers to the weight in pounds of the amount of kernels contained in a bushel unit of volume.

Tissue culture: A composition that includes isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, ovules, pericarp, flowers, florets, heads, spikelets, seeds, leaves, stems, roots, root tips, anthers, pistils, awns, stems, and the like.

Transformation. The introduction of new genetic material (e.g., exogenous transgenes) into plant cells. Exemplary mechanisms that are to transfer DNA into plant cells include (but not limited to) electroporation, microprojectile bombardment, *Agrobacterium*-mediated transformation and direct DNA uptake by protoplasts.

Transgene. A gene or genetic material that has been transferred into the genome of a plant, for example by genetic engineering methods. Exemplary transgenes include cDNA (complementary DNA) segment, which is a copy of mRNA (messenger RNA), and the gene itself residing in its original region of genomic DNA. In one example, describes a segment of DNA containing a gene sequence that is introduced into the genome of a wheat plant or plant cell. This non-native segment of DNA may retain the ability to produce RNA or protein in the transgenic plant, or it may alter the normal function of the transgenic plant's genetic code. In general, the transferred nucleic acid is incorporated into the plant's germ line. Transgene can also describe any DNA sequence, regardless of whether it contains a gene coding sequence or it has been artificially constructed, which has been introduced into a plant or vector construct in which it was previously not found.

New Wheat Resistant to Leaf Rust, Stem Rust, Stripe Rust, Soil-Borne Mosaic Virus, Powdery Mildew, and Hessian Flies The present disclosure relates to a new wheat cultivar, 'GA 04570-10E46'. This new variety is a medium maturing variety with high yield and excellent test weight, and is resistant to many pests that affect wheat including leaf rust (e.g., races MCTNB, TDBGG, TBBGJ, TNRJ, MCDS, KFBJ, MLDS, TCRKG, TFBJ, and TCTSB), stem rust (e.g., stem rust races, QFCSC, QTHJC, RCRSC, RKQQC, TTTTF, SCCSC, and QCCSM), stripe rust, soil-borne mosaic virus, powdery mildew, and Hessian flies. The new cultivar also has acceptable milling and baking quality characteristics. The new variety is adapted to areas of the United States (such as the southern and southeastern United States), such as areas that are known to have or expected to have damaging levels of leaf rust (e.g., races MCTNB, TDBGG, TBBGJ, TNRJ, MCDS, KFBJ, MLDS, TCRKG, TFBJ, and TCTSB), stem rust (e.g., stem rust races, QFCSC, QTHJC, RCRSC, RKQQC, TTTTF, SCCSC, and QCCSM), stripe rust, soil-borne mosaic virus, powdery mildew, Hessian flies.

Thus provided herein is a seed of wheat variety 'GA 04570-10E46', wherein representative sample seed of the variety is deposited under (ATCC Accession No. PTA-123659). Also provided are bulk wheat seed containing such seeds. The disclosure provides wheat plants having or consisting of the morphological and physiological characteristics of 'GA 04570-10E46'. The disclosure also provides wheat plants having one or more of (such as at least two, at least three, at least four, at least five, at least 6, at least 7, at least 8, at least 8 or at least 10 of) the morphological and physiological characteristics of 'GA 04570-10E46' (such as those listed in Tables 1-15). In one example, such plants have or include the characteristics noted in Tables 1-15, for example at least five of medium maturing, high yield, excellent test weight, resistance to leaf rust (e.g., races MCTNB, TDBGG, TBBGJ, TNRJ, MCDS, KFBJ, MLDS, TCRKG, TFBJ, and TCTSB), resistance to stem rust (e.g., stem rust races, QFCSC, QTHJC, RCRSC, RKQQC, TTTTF, SCCSC, and QCCSM), resistance to stripe rust, resistance to soil-borne mosaic virus, resistance to powdery mildew, resistance to Hessian flies, and acceptable milling and baking quality characteristics. Also provided are seeds of such plants, progeny of such plants, parts of such plants (such as pollen, ovules and cells). In one example, the disclosure provides wheat plants having the genotype of 'GA 04570-10E46'. For example, the disclosure provides plants produced by growing the seed of the new wheat cultivar 'GA 04570-10E46'.

The disclosed 'GA 04570-10E46' plants, and in some examples progeny thereof, have increased grain yield as compared to other medium maturing wheat, such as 'AGS 2035' and 'Baldwin'. For example, the disclosed 'GA 04570-10E46' plants, and in some examples progeny thereof, have a grain yield of at least 60 bu/a. In some examples, the disclosed 'GA 04570-10E46' plants, and in some examples progeny thereof, have a seed yield that is at least 5%, at least 6%, at least 7%, at least 8%, at least 9%, at least 10%, or at least 12% greater than another medium maturing wheat, such as 'AGS 2035' and 'Baldwin'.

In some examples, the disclosed 'GA 04570-10E46' plants, and in some examples progeny thereof, have a disease rating for resistance to leaf rust of no more than 0.6, no more than 0.5, or no more than 0.5 (such as 0 to 0.6, 0 to 0.4, 0.2 to 0.5, or 0 to 0.5), have a disease rating for resistance to stripe rust of no more than 2, no more than 1.5, or no more than 1 (such as 0 to 2, 0 to 0.5, or 0 to 1), have a disease rating for resistance to soil-borne mosaic virus of no more than 0.5, no more than 0.3, or no more than 0.2 (such as 0 to 0.5, 0 to 0.2 or 0 to 0.1), have a disease rating for resistance to powdery mildew of no more than 2, no more than 1.8, or no more than 1.5 (such as 0.2 to 2, 0.2 to 1.5, 0.2 to 1.4, 0.2 to 1.3, 0 to 0.5, or 0 to 1.5), have a disease rating for resistance to Hessian fly of no more than 5, no more than 4, or no more than 2 (such as 0 to 5, 0 to 2 or 0 to 3), is resistant to stem rust, or combinations thereof.

The disclosed 'GA 04570-10E46' plants and seeds can be used to produce other wheat plants and seeds, for example as part of a breeding program. Choice of breeding or selection methods using to generate new wheat plants and seeds can depend on the mode of plant reproduction, the heritability of the trait(s) being improved, and the type of variety used commercially (e.g., $F_1$ hybrid variety, pureline variety, etc.). For highly heritable traits, a choice of superior individual plants evaluated at a single location can be effective, whereas for traits with low heritability, selection can be based on mean values obtained from replicated evaluations of families of related plants. Popular selection methods commonly include pedigree selection, modified pedigree selection, mass selection, recurrent selection and backcrossing.

The complexity of inheritance influences choice of the breeding method. Backcross breeding can be used to transfer one or a few favorable genes for a highly heritable trait into a desirable variety. This approach has been used extensively for breeding disease-resistant varieties (e.g., see Bowers et al., 1992. Crop Sci. 32(1):67-72; Nickell and Bernard, 1992. Crop Sci. 32(3):835). Various recurrent selection techniques can be used to improve quantitatively inherited traits controlled by numerous genes.

Promising advanced breeding lines can be thoroughly tested and compared to appropriate standards in environments representative of the commercial target area(s) for generally three or more years. The best or most preferred lines are candidates for new commercial varieties. Those still deficient in a few traits may be used as parents to produce new populations for further selection.

A difficult task is the identification of individuals that are genetically superior, because for most traits the true genotypic value can be masked by other confounding plant traits or environmental factors. One method of identifying a superior plant is to observe its performance relative to other experimental plants and to one or more widely grown standard varieties. Single observations can be generally inconclusive, while replicated observations provide a better estimate of genetic worth.

Plant breeding can result in new, unique and superior wheat varieties and hybrids from 'GA 04570-10E46'. Two or more parental lines can be selected (such as 'GA 04570-10E46' as one of the lines), followed by repeated selfing and selection, producing many new genetic combinations. Each year, the germplasm to advance to the next generation is selected. This germplasm is grown under unique and different geographical, climatic and soil conditions, and further selections are then made, during and at the end of the growing season. The varieties developed can be unpredictable, because the selection occurs in unique environments, with no control at the DNA level (using conventional breeding procedures), and with millions of different possible genetic combinations being generated.

The development of new wheat varieties from 'GA 04570-10E46' involves the development and selection of wheat varieties, the crossing of these varieties and selection of progeny from the superior hybrid crosses. A hybrid seed is produced by manual crosses between selected male-fertile parents or by using male sterility systems. Hybrids can be identified by using certain single locus traits, which indicate that the seed is truly a hybrid. Additional data on parental lines as well as the phenotype of the hybrid can influence a decision whether to continue with the specific hybrid cross.

Pedigree breeding and recurrent selection breeding methods can be used to develop varieties from breeding populations. Breeding programs combine desirable traits from two or more varieties or various broad-based sources into breeding pools from which varieties are developed by selfing and selection of desired phenotypes. Pedigree breeding is commonly used for the improvement of self-pollinating crops. Two parents (e.g., wherein one of the parents is 'GA 04570-10E46') which possess favorable, complementary traits are crossed to produce an $F_1$. An F2 population is produced by selfing one or several $F_1$'s. Selection of the best or most preferred individuals can begin in the $F_2$ population (or later depending upon the breeding objectives); then, beginning in the $F_3$, the best or most preferred individuals in the best families can be selected. Replicated testing of families can begin in the $F_3$ or $F_4$ generation to improve the effectiveness of selection for traits with low heritability. At an advanced stage of inbreeding (i.e., $F_6$ and $F_7$), the best lines or mixtures of phenotypically similar lines can be tested for potential commercial release as new varieties.

Mass and recurrent selections can be used to improve populations of either self- or cross-pollinating crops. A genetically variable population of heterozygous individuals is either identified or created by intercrossing several different parents. The best or most preferred plants are selected based on individual superiority, outstanding progeny, or excellent combining ability. The selected plants are intercrossed to produce a new population in which further cycles of selection are continued.

Backcross breeding has been used to transfer genetic loci for simply inherited, highly heritable traits into a desirable homozygous variety which is the recurrent parent (e.g., 'GA 04570-10E46'). The source of the trait to be transferred is called the donor or nonrecurrent parent. The resulting plant is typically expected to have the attributes of the recurrent parent (e.g., variety) and the desirable trait transferred from the donor parent. After the initial cross, individuals possessing the phenotype of the donor parent are selected and repeatedly crossed (backcrossed) to the recurrent parent. The resulting plant is typically expected to have the attributes of the recurrent parent (e.g., variety) and the desirable trait transferred from the donor parent.

The single-seed descent procedure can refer to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population are represented by a progeny when generation advance is completed.

In a multiple-seed procedure, one or more seeds from each plant in a population are commonly harvested and threshed together to form a bulk. Part of the bulk is used to plant the next generation and part is put in reserve. The procedure has been referred to as modified single-seed descent. The multiple-seed procedure has been used to save labor at harvest. It is considerably faster to thresh pods with a machine than to remove one seed from each by hand for the single-seed procedure. The multiple-seed procedure also makes it possible to plant the same number of seeds of a population each generation of inbreeding. Sufficient numbers of seeds are harvested to make up for those plants that did not germinate or produce seed.

Descriptions of other breeding methods that are commonly used for different traits and crops can be found in one of several reference books (e.g., Allard. 1960. Principles of plant breeding. Davis, Calif.: John Wiley & Sons, NY, University of California, pp. 50-98; Simmonds. 1979. Principles of crop improvement. New York: Longman, Inc., pp. 369-399; Sneep and Hendriksen. 1979. "Plant breeding perspectives." Wageningen (ed.), Center for Agricultural Publishing and Documentation; Fehr. 1987.

Breeding Wheat Cultivar 'GA 04570-10E46'

Methods for crossing the new wheat cultivar 'GA 04570-10E46' with itself or a second plant are provided, as are the seeds and plants produced by such methods. Such methods can be used for propagation of the new wheat variety 'GA 04570-10E46', or can be used to produce hybrid wheat seeds and the plants grown therefrom. Hybrid wheat plants can be used, for example, in the commercial production of grain products or in breeding programs for the production of novel wheat varieties. A hybrid plant can also be used as a recurrent parent at any given stage in a backcrossing protocol during the production of a single locus conversion (for example introduction of one or more desirable traits) of the new wheat variety 'GA 04570-10E46'.

Methods are provided for producing a wheat plant by crossing a first parent wheat plant with a second parent wheat plant wherein either the first or second parent wheat plant is variety 'GA 04570-10E46'. The other parent may be any other wheat plant, such as a wheat plant that is part of a synthetic or natural population. Any such methods using wheat variety 'GA 04570-10E46' can be used, such as selfing, sibbing, backcrosses, recurrent selection, mass selection, pedigree breeding, bulk selection, hybrid production, mutation breeding, and crosses to populations.

Methods of producing wheat plants and/or seed are provided. Such a method can include crossing the new wheat cultivar 'GA 04570-10E46' with itself or a second wheat plant and harvesting a resulting wheat seed, such as an $F_1$ hybrid seed. The resulting plant can be grown, resulting in a wheat plant or part thereof.

In one example methods of producing an inbred wheat plant derived from wheat variety 'GA 04570-10E46' are provided. In one example such methods include (a) preparing a progeny plant derived from wheat cultivar 'GA 04570-10E46' by crossing a plant of the wheat cultivar 'GA 04570-10E46' with a wheat plant of a second variety; (b) crossing the progeny plant with itself or a second plant to produce a seed of a progeny plant of a subsequent generation; (c) growing a progeny plant of a subsequent generation from said seed and crossing the progeny plant of a subsequent generation with itself or a second plant; and (d) repeating steps (b) and (c) for an additional at least 2 generations (such as at least 3, at least 4, at least 5, at least 6, at least 7, at least 8 at least 9, at least 10, at least 15 or at least 20, such as 2 to 10, 3 to 10, or 3 to 15 generations) with sufficient inbreeding to produce an inbred wheat plant derived from the wheat cultivar 'GA 04570-10E46'.

The second plant crossed with the new wheat cultivar 'GA 04570-10E46' for the purpose of developing novel wheat varieties, is typically a plant which either themselves exhibit one or more desirable characteristics or which exhibit one or more desired characteristic(s) when in hybrid combination. In one example, the second wheat plant is transgenic. Exemplary desired characteristics include, but are not limited to: increased seed yield, increased seedling vigor, modified maturity date, desired plant height, herbicide tolerance, drought tolerance, heat tolerance, low or high soil pH level tolerance, salt tolerance, resistance to an insect, resistance to a bacterial disease, resistance to a viral disease, resistance to a fungal disease, resistance to a nematode, resistance to a pest, male sterility, site-specific recombination; abiotic stress tolerance; modified phosphorus characteristics; modified antioxidant characteristics; modified essential seed amino acid characteristics; modified fatty acid metabolism, modified carbohydrate metabolism, and decreased phytate.

When the new wheat cultivar 'GA 04570-10E46' is crossed with another different variety, first generation ($F_1$) wheat progeny are produced. The hybrid progeny are produced regardless of characteristics of the two varieties produced. As such, an $F_1$ hybrid wheat plant can be produced by crossing 'GA 04570-10E46' with any second wheat plant. The second wheat plant can be genetically homogeneous (e.g., inbred) or can itself be a hybrid. Therefore the disclosure provides any $F_1$ hybrid wheat plant produced by crossing the new wheat cultivar 'GA 04570-10E46' with a second wheat plant (such as a transgenic plant having one or more genes that confer to the plant one or more desired characteristics).

Wheat plants can be crossed by either natural or mechanical techniques. Natural pollination can occur by self-pollination or natural cross pollination, which typically is aided by pollinating organisms.

Wheat varieties such as 'GA 04570-10E46' can be used in seed and grain production. However, wheat varieties such as 'GA 04570-10E46' also provide a source of breeding material that may be used to develop new wheat varieties. Plant breeding techniques known in the art and used in a wheat plant breeding program include, but are not limited to, recurrent selection, mass selection, bulk selection, mass selection, backcrossing, pedigree breeding, open pollination breeding, restriction fragment length polymorphism enhanced selection, genetic marker enhanced selection, making double haploids, and transformation. Often, combinations of these techniques are used. The development of wheat varieties in a plant breeding program requires, in general, the development and evaluation of homozygous varieties. There are many analytical methods available to evaluate a new variety. Observation of phenotypic traits but genotypic analysis may also be used.

Expression Vectors for Wheat Transformation

Various genetic elements can be introduced into a wheat plant genome using transformation. These elements include, but are not limited to genes, coding sequences, inducible, constitutive, and tissue specific promoters, enhancing sequences, and signal and targeting sequences.

Exemplary Marker Genes

Expression vectors include at least one genetic marker operably linked to a regulatory element that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. Positive selection methods are also known in the art.

One exemplary selectable marker gene for plant transformation is the neomycin phosphotransferase II (nptII), which when under the control of plant regulatory signals, confers resistance to kanamycin. Another exemplary selectable marker gene is the hygromycin phosphotransferase gene, which confers resistance to the antibiotic hygromycin.

Additional selectable marker genes of bacterial origin that confer resistance to antibiotics include gentamycin acetyl transferase, streptomycin phosphotransferase, and aminoglycoside-3'-adenyl transferase, the bleomycin resistance determinant. Other selectable marker genes confer tolerance or resistance to herbicides such as glyphosate, glufosinate or bromoxynil.

Other selectable marker genes for plant transformation that are not of bacterial origin include, for example, mouse dihydrofolate reductase, plant 5-enolpyruvyl-shikimate-3-phosphate synthase and plant acetolactate synthase.

Another class of marker genes for plant transformation requires screening of presumptively transformed plant cells, rather than direct genetic selection of transformed cells, for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include beta glucuronidase (GUS), beta-galactosidase, luciferase and chloramphenicol acetyltransferase. Methods for visualizing GUS activity that do not require destruction of plant tissue are also available.

Green Fluorescent Protein (GFP) can be utilized as a marker for gene expression. GFP and mutants of GFP can be used as screenable markers.

Exemplary Promoters

Genes included in expression vectors are driven by a nucleotide sequence comprising a regulatory element, for example, a promoter. Several types of promoters are well known, as are other regulatory elements that can be used alone or in combination with promoters.

A "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may affect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

An inducible promoter is operably linked to a gene for expression in wheat. Optionally, the inducible promoter is operably linked to a nucleotide sequence encoding a signal sequence which is operably linked to a gene for expression in wheat. With an inducible promoter, the rate of transcription increases in response to an inducing agent. Any inducible promoter can be used in the disclosed methods. Exemplary inducible promoters include, but are not limited to, those from the ACEI system, which respond to copper; In2 gene from maize, which responds to benzenesulfonamide herbicide safeners. In an embodiment, the inducible promoter is a promoter that responds to an inducing agent to which plants do not normally respond. An exemplary inducible promoter is the inducible promoter from a steroid hormone gene, the transcriptional activity of which is induced by a glucocorticosteroid hormone.

A constitutive promoter is operably linked to a gene for expression in wheat or is operably linked to a nucleotide sequence encoding a signal sequence which is operably linked to a gene for expression in wheat. Many different constitutive promoters can be utilized. Exemplary constitutive promoters include, but are not limited to, the promoters from plant viruses such as the 35S promoter from CaMV and the promoters from such genes as rice actin; ubiquitin; pEMU; MAS and maize H3 histone. The ALS promoter, XbaI/NcoI fragment 5' to the *Brassica napus* ALS3 structural gene (or a nucleotide sequence similarity to said XbaI/NcoI fragment), can be used.

A tissue-specific promoter can be operably linked to a gene for expression in wheat. Optionally, the tissue-specific promoter is operably linked to a nucleotide sequence encoding a signal sequence which is operably linked to a gene for expression in wheat. Plants transformed with a gene of interest operably linked to a tissue-specific promoter may produce the protein product of the transgene exclusively, or preferentially, in a specific tissue. Any tissue-specific or tissue-preferred promoter can be utilized. Exemplary tissue-specific or tissue-preferred promoters include, but are not limited to, a root-preferred promoter, such as that from the phaseolin gene; a leaf-specific and light-induced promoter, such as that from cab or rubisco; an anther-specific promoter, such as that from LAT52; a pollen-specific promoter, such as that from Zm13; or a microspore-preferred promoter, such as that from apg.

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized. The presence of a signal sequence directs a polypeptide to either an intracellular organelle or subcellular compartment or for secretion to the apoplast. Many signal sequences are known in the art.

Wheat Plants Having One or More Desired Heritable Traits

The disclosure provides plants of the new wheat cultivar 'GA 04570-10E46' modified to include one or more desired heritable traits. In some examples, such plants can be developed using backcrossing or genetic engineering (such as direct transformation, for example by introducing one or more transgenes into the 'GA 04570-10E46' variety, wherein the transgenes encode one or more desired traits), wherein essentially all of the desired morphological and physiological characteristics of the 'GA 04570-10E46' variety are recovered (such as 2, 3, 4, 5, 6, 7, 8, 9, or all 10 of medium maturing, high yield, excellent test weight, resistance to leaf rust (e.g., races MCTNB, TDBGG, TBBGJ, TNRJ, MCDS, KFBJ, MLDS, TCRKG, TFBJ, and TCTSB), resistance to stem rust (e.g., stem rust races, QFCSC, QTHJC, RCRSC, RKQQC, TTTTF, SCCSC, and QCCSM), resistance to stripe rust, resistance to soil-borne mosaic virus, resistance to powdery mildew, resistance to Hessian flies, and acceptable milling and baking quality characteristics) in addition to a genetic locus transferred into the plant via the backcrossing technique. The term backcross conversion and single locus conversion are used interchangeably to designate the product of a backcrossing program. Plants developed using such methods can be referred to as a single locus converted plant.

A transgenic variant of 'GA 04570-10E46' may contain at least one transgene but could contain at least 1, 2, 3, 4, 5, 6, 7, 8, 9, 10, or more transgenes. In another embodiment, a transgenic variant of 'GA 04570-10E46' contains no more than 15, 14, 13, 12, 11, 10, 9, 8, 7, 6, 5, 4, 3, or 2 transgenes.

In one example, the method of introducing one or more desired traits into wheat cultivar 'GA 04570-10E46' includes (a) crossing a plant of variety 'GA 04570-10E46' with a second plant having one or more desired traits to produce $F_1$ progeny plants; (b) selecting $F_1$ progeny plants that have the one or more desired traits to produce selected $F_1$ progeny plants; (c) crossing the selected progeny plants with at least a first plant of variety 'GA 04570-10E46' to produce backcross progeny plants; (d) selecting backcross progeny plants that have the one or more desired traits and physiological and morphological characteristics of wheat variety 'GA 04570-10E46' to produce selected backcross progeny plants; and (e) repeating steps (c) and (d) one or more times in succession to produce selected second or higher backcross progeny plants that have the one or more desired traits and the physiological and morphological characteristics of wheat cultivar 'GA 04570-10E46' when grown in the same environmental conditions.

In some embodiments, a 'GA 04570-10E46' plant which has been developed using both genetic engineering and traditional breeding techniques. For example, a genetic trait may have been engineered into the genome of a particular wheat plant may then be moved into the genome of a 'GA 04570-10E46' plant using traditional breeding techniques that are well known in the plant breeding arts. Likewise, a genetic trait may have been engineered into the genome of a 'GA 04570-10E46' wheat plant may then be moved into the genome of another variety using traditional breeding techniques. A backcrossing approach is commonly used to move a transgene from a transformed wheat variety into an already developed wheat variety, and the resulting backcross conversion plant would then comprise the transgene(s).

Plant transformation involves the construction of an expression vector that will function in plant cells. Such a vector can include DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed wheat plants, using transformation methods to incorporate transgenes into the genetic material of the wheat plant(s).

Using the disclosed transgenic wheat plants, a foreign protein can be produced in commercial quantities. Thus, techniques for the selection and propagation of transformed plants, yield a plurality of transgenic plants which are harvested in a conventional manner. A foreign protein can then be extracted from a tissue of interest or from total biomass. Protein extraction from plant biomass can be accomplished by known methods. The transgenic plant for commercial production of foreign protein is, or is derived from a 'GA 04570-10E46' wheat plant. In one embodiment, the biomass of interest is or is derived from a 'GA 04570-10E46' seed. For the transgenic plants that show higher levels of expression, a genetic map can be generated, e.g., via conventional restriction fragment length polymorphism (RFLP), polymerase chain reaction (PCR) and simple sequence repeat (SSR) analysis, which identifies the approximate chromosomal location of the integrated DNA molecule. Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons can involve hybridizations, RFLP, PCR, SSR and sequencing, all of which are conventional techniques.

Transformed 'GA 04570-10E46' plants that express particular agronomic genes or phenotypes of agronomic interest are provided. Exemplary genes include, but are not limited to, those provided herein.

Backcrossing Methods

Backcrossing methods can be used to improve or introduce a characteristic into the new wheat cultivar 'GA 04570-10E46' (for example using the methods provided in U.S. Pat. No. 6,140,556). Both naturally occurring and transgenic DNA sequences may be introduced through backcrossing techniques. In some embodiments, the number of loci that may be backcrossed into 'GA 04570-10E46' is at least 1, 2, 3, 4, 5, 6, 7, 8, 9, 10, or more. A single locus may contain several transgenes. The backcross conversion can result from either the transfer of a dominant allele or a recessive allele. Selection of progeny containing the trait of interest is accomplished by direct selection for a trait associated with a dominant allele.

For example, a variety may be backcrossed 1, 2, 3, 4, 5, 6, 7, 8, 9 or more times to the recurrent parent. The parental wheat plant which contributes the locus for the desired characteristic is termed the "nonrecurrent" or "donor" parent. This terminology refers to the fact that the nonrecurrent parent is used one time in the backcross protocol and therefore does not recur. The parental wheat plant to which the locus or loci from the nonrecurrent parent are transferred is known as the recurrent parent as it is used for several rounds in the backcrossing protocol. In a typical backcross protocol, the original variety of interest (recurrent parent, e.g., 'GA 04570-10E46') is crossed to a second variety (nonrecurrent parent) that carries the single locus of interest (such as a desirable trait) to be transferred. The resulting progeny from this cross are then crossed again to the recurrent parent and the process is repeated until a wheat plant is obtained wherein essentially all of the desired morphological and physiological characteristics of the recurrent parent (e.g., 'GA 04570-10E46') are recovered (such as medium maturing, high yield, excellent test weight, resistance to leaf rust (e.g., races MCTNB, TDBGG, TBBGJ, TNRJ, MCDS, KFBJ, MLDS, TCRKG, TFBJ, and TCTSB), resistance to stem rust (e.g., stem rust races, QFCSC, QTHJC, RCRSC, RKQQC, TTTTF, SCCSC, and QCCSM), resistance to stripe rust, resistance to soil-borne mosaic virus, resistance to powdery mildew, resistance to Hessian flies, and acceptable milling and baking quality characteristics) in the converted plant, in addition to the single transferred locus from the nonrecurrent parent.

The goal of a backcross protocol is to alter or substitute a single trait or characteristic in the original variety, such as 'GA 04570-10E46'. To accomplish this, a single locus of the recurrent variety is modified or substituted with the desired locus from the nonrecurrent parent, while retaining essentially all of the rest of the desired genetic traits, and therefore the desired physiological and morphological constitution of the original variety. The choice of the particular nonrecurrent parent can depend on the purpose of the backcross; for example, a major purpose is to add a commercially desirable, agronomically important trait to the plant. The exact backcrossing protocol can depend on the characteristic or trait being altered to determine an appropriate testing protocol. Although backcrossing methods are simplified when the characteristic being transferred is a dominant allele, a recessive allele can also be transferred. In this instance, it can be useful to introduce a test of the progeny to determine if the desired characteristic has been successfully transferred.

In a backcross where the desired characteristic being transferred to the recurrent parent is controlled by a major gene which can be readily evaluated during the backcrossing, it is common to conduct enough backcrosses to avoid testing individual progeny for specific traits such as yield in extensive replicated tests. In general, four or more backcrosses are used when there is no evaluation of the progeny for specific traits, such as yield o resistance to a pest. As in this example, lines with the phenotype of the recurrent parent can be composited without the usual replicated tests for traits such as yield, protein or oil percentage in the individual lines.

Wheat varieties can also be developed from more than two parents, for example using modified backcrossing, which uses different recurrent parents during the backcrossing. Modified backcrossing can be used to replace the original recurrent parent with a variety having certain more desirable characteristics, or multiple parents can be used to obtain different desirable characteristics from each.

Many single locus traits are known that are not regularly selected for in the development of a new inbred but that can be improved by backcrossing techniques. Single locus traits can be, but are not necessarily, transgenic. Examples of these traits include, but are not limited to, male sterility, waxy starch, herbicide tolerance or resistance, resistance for bacterial, fungal, or viral disease, insect resistance or tolerance, male fertility, enhanced nutritional quality, industrial usage, yield stability and yield enhancement. These comprise genes generally inherited through the nucleus. Thus plants of wheat variety 'GA 04570-10E46' that include a single locus conversion (such as one that confers a desired trait) are provided herein.

Direct selection can be applied where the single locus acts as a dominant trait. An example of a dominant trait is the herbicide resistance trait (such as glyphosate resistance). For the selection process, the progeny of the initial cross are sprayed with an herbicide (such as Roundup®) prior to the backcrossing. The spraying eliminates any plants which do not have the desired herbicide resistance characteristic; only those plants which have the herbicide resistance gene are used in the subsequent backcross. This process is then repeated for all additional backcross generations.

Genetic Markers

Selection of wheat plants for breeding may not be dependent on the phenotype of a plant and instead can be based on genetic investigations. For example, a suitable genetic marker can be used which is closely genetically linked to a desired trait. One of these markers can therefore be used to identify the presence or absence of a trait in the offspring of a particular cross, and hence can be used in selection of progeny for continued breeding. This technique is referred to as marker assisted selection. Any other type of genetic marker or other assay which is able to identify the relative presence or absence of a trait of interest in a plant can also be useful for breeding. Procedures for marker assisted selection applicable to the breeding of wheat are well known in the art. Such methods can be useful in the case of recessive traits and variable phenotypes, or where conventional assays are more expensive, time consuming or otherwise disadvantageous. Types of genetic markers which can be used, but are not limited to, Simple Sequence Length Polymorphisms (SSLPs), Restriction Fragment Length Polymorphisms (RFLPs), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858), Single Nucleotide Polymorphisms (SNPs), and Simple Sequence Repeats (SSRs) which are also referred to as Microsatellites.

Particular markers used for these purposes are not limited to any particular set of markers, but are envisioned to include any type of marker and marker profile which provides a means of distinguishing varieties. One method of comparison is to use only homozygous loci for 'GA 04570-10E46'. In addition to being used for identification of wheat variety 'GA 04570-10E46' and plant parts and plant cells of variety 'GA 04570-10E46', the genetic profile may be used to identify a wheat plant produced through the use of 'GA 04570-10E46' or to verify a pedigree for progeny plants produced through the use of 'GA 04570-10E46'. The genetic marker profile is also useful in breeding and developing backcross conversions. In some embodiments, the present disclosure provides comprises a wheat plant characterized by molecular and physiological data obtained from the representative sample of 'GA 04570-10E46', deposited with the American Type Culture Collection (ATCC). Also provided is a wheat plant formed by the combination of the 'GA 04570-10E46' plant or plant cell with another wheat plant or cell and comprising the homozygous alleles of the variety.

Plants and plant parts substantially benefiting from the use of 'GA 04570-10E46' in their development, such as 'GA 04570-10E46' comprising a backcross conversion, transgene, or genetic sterility factor, may be identified by having a molecular marker profile with a high percent identity to 'GA 04570-10E46', such as at least 95%, 96%, 97%, 98%, 99%, 99.5% or 99.9% identity to 'GA 04570-10E46'.

In one example, the SSR (or other genetic marker) profile of 'GA 04570-10E46' also can be used to identify essentially derived varieties and other progeny varieties developed from the use of 'GA 04570-10E46', as well as cells and other plant parts thereof. Progeny plants and plant parts produced using 'GA 04570-10E46' may be identified by having a molecular marker profile of at least 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.5% genetic contribution from 'GA 04570-10E46', as measured by either percent identity or percent similarity. Such progeny may be further characterized as being within a pedigree distance of 'GA 04570-10E46', such as within 1, 2, 3, 4 or 5 or fewer cross-pollinations to a wheat plant other than 'GA 04570-10E46' or a plant that has 'GA 04570-10E46' as a progenitor. Unique molecular profiles may be identified with other molecular tools such as SNPs and RFLPs.

While determining a SSR (or other) genetic marker profile of the plants, several unique profiles may also be identified which did not appear in either parent of such plant. Such unique profiles may arise during the breeding process from recombination or mutation. A combination of several unique alleles provides a means of identifying a plant variety, an $F_1$ progeny produced from such variety, and further progeny produced from such variety.

Useful or desirable traits can be introduced by backcrossing, as well as directly into a plant by genetic transformation methods. Genetic transformation can therefore be used to insert a selected transgene into the 'GA 04570-10E46' variety or can, alternatively, be used for the preparation of transgenes which can be introduced by backcrossing. Thus, the disclosure provides methods of producing a plant of wheat variety 'GA 04570-10E46' that includes one or more added desired traits, for example that include introducing a transgene(s) conferring the one or more desired traits into a plant of wheat cultivar 'GA 04570-10E46' (for example by transformation with a transgene that confers upon the wheat plant the desired trait), thereby producing a plant of wheat variety 'GA 04570-10E46' that includes the one or more added desired traits.

Methods of Transformation

Methods for the transformation of many economically important plants, including wheat, are well known. Methods for introducing a desired nucleic acid molecule (e.g., transgene), such as DNA (e.g., cDNA), RNA, or inhibitory RNAs, are well known in the art, and the disclosure is not limited to particular methods. Exemplary methods include biological and physical plant transformation protocols. In addition, expression vectors and in vitro culture methods for plant cell or tissue transformation and regeneration of plants are available. Exemplary techniques which can be employed for the genetic transformation of wheat include, but are not limited to, electroporation (e.g., of protoplasts and whole cells and tissues), sonication, microprojectile bombardment, liposome and spheroplast fusion, *Agrobacterium*-mediated transformation and direct DNA uptake by protoplasts (e.g., using $CaCl_2$ precipitation, polyvinyl alcohol or poly-L-ornithine).

To effect transformation by electroporation, friable tissues, such as a suspension culture of cells or embryogenic callus, can be used. Alternatively, immature embryos or other organized tissue can be transformed directly. In this technique, the cell walls of target cells can be partially degraded by exposing them to pectin-degrading enzymes (pectolyases) or mechanically wound tissues in a controlled manner.

Protoplasts can also be employed for electroporation transformation of plants (Bates. 1994. *Mol. Biotechnol.* 2(2):135-145; Lazzeri. 1995. *Methods Mol. Biol.* 49:95-106).

In microprojectile bombardment, particles (such as those comprised of tungsten, platinum, or gold) are coated with nucleic acids and delivered into cells by a propelling force. For the bombardment, cells in suspension are concentrated on filters or solid culture medium. Alternatively, immature embryos or other target cells can be arranged on solid culture medium. The cells to be bombarded are positioned at an appropriate distance below the macroprojectile stopping plate. An exemplary method for delivering DNA into plant cells by acceleration is the Biolistics Particle Delivery System, which can be used to propel particles coated with DNA or cells through a screen, such as a stainless steel or Nytex screen, onto a surface covered with target wheat cells. The screen disperses the particles so that they are not delivered to the recipient cells in large aggregates. A screen intervening between the projectile apparatus and the cells to be bombarded can reduce the size of projectiles aggregate and contribute to a higher frequency of transformation by reducing the damage inflicted on the recipient cells by projectiles that are too large. Microprojectile bombardment methods can be used to transform wheat, as described, for example, in U.S. Pat. No. 5,322,783.

*Agrobacterium*-mediated transfer is a well-known method in the art for introducing gene loci into plant cells. DNA can be introduced into whole plant tissues, thereby bypassing the need for regeneration of an intact plant from a protoplast. *Agrobacterium* transformation vectors are capable of replication in *E. coli* as well as *Agrobacterium*, allowing for convenient manipulations (Klee et al. 1985. *Bio. Tech.* 3(7):637-342). Moreover, vectors for *Agrobacterium*-mediated gene transfer have improved the arrangement of genes and restriction sites in the vectors to facilitate the construction of vectors capable of expressing various polypeptide coding genes. Such vectors have convenient multi-linker regions flanked by a promoter and a polyadenylation site for direct expression of inserted polypeptide coding genes. Additionally, *Agrobacterium* containing both armed and disarmed Ti genes can be used for transformation. The use of *Agrobacterium*-mediated plant integrating vectors to introduce DNA into plant cells is well known (e.g., Fraley et al. 1985. *Bio. Tech.* 3(7):629-635; U.S. Pat. No. 5,563,055). Briefly, plant tissue (often leaves) is cut into small pieces, e.g. 10 mm×10 mm, and soaked for 10 minutes in a fluid containing suspended *Agrobacterium*. Some cells along the cut will be transformed by the bacterium, which inserts its DNA into the cell, which is placed on selectable rooting and shooting media, allowing the plants to regrow. Some plants can be transformed just by dipping the flowers into suspension of *Agrobacterium* and then planting the seeds in a selective medium.

Transformation of plant protoplasts can also be achieved using methods based on calcium phosphate precipitation, polyethylene glycol treatment, electroporation, and combinations of these treatments (e.g., Potrykus et al. 1985. *Mol. Gen. Genet.* 199(2):169-177; Omirulleh et al. 1993. *Plant Mol. Biol.* 21(3):415-428; Fromm et al. 1986. *Nature.* 319 (6056):791-739; Uchimiya et al. 1986. *Mol. Gen. Genet.* 204(2):207-207; Marcotte et al. 1988. *Nature* 335(6189): 454-457). The ability to regenerate wheat plants from protoplasts makes these techniques applicable to wheat (Dhir et al. 1991. *Plant Cell Rep.* 10(2):97-101).

In one example, such methods can also be used to introduce transgenes for the production of proteins in transgenic wheat. The resulting produced protein can be harvested from the transgenic wheat. The transgene can be harvested from the transgenic plants that are originated or are descended from the new wheat variety 'GA 04570-10E46', a seed of 'GA 04570-10E46' or a hybrid progeny of 'GA 04570-10E46'.

Numerous different genes are known and can be introduced into a wheat plant 'GA 04570-10E46' or progeny thereof. Non-limiting examples of particular genes and corresponding phenotypes that can be chosen for introduction into a wheat plant are provided herein. In some examples, any combination of the genes/characteristics described herein are introduced into 'GA 04570-10E46' or its progeny.

The foregoing methods for transformation would typically be used for producing a transgenic variety. The transgenic variety could then be crossed, with another (non-transformed or transformed) variety, in order to produce a new transgenic variety. Alternatively, a genetic trait which has been engineered into a particular wheat cultivar using the foregoing transformation techniques could be moved into another cultivar using traditional backcrossing techniques. For example, a backcrossing approach could be used to move an engineered trait from a public, non-elite variety into an elite variety, or from a variety containing a foreign gene in its genome into a variety or varieties which do not contain that gene. As used herein, "crossing" can refer to a simple X by Y cross, or the process of backcrossing, depending on the context.

Following transformation of wheat target tissues, expression of a selectable marker gene(s) allows for preferential selection of transformed cells, tissues and/or plants, using regeneration and selection methods now well known in the art.

Herbicide Resistance

Numerous herbicide resistance genes are known and can be used with the methods and plants provided herein. In particular examples, a herbicide resistance gene confers tolerance to an herbicide comprising glyphosate, sulfonylurea, imidazalinone, dicamba, glufosinate, phenoxy proprionic acid, cyclohexone, triazine, benzonitrile, broxynil, L-phosphinothricin, cyclohexanedione, chlorophenoxy acetic acid, or combinations thereof.

In one example the herbicide resistance gene is a gene that confers resistance to a herbicide that inhibits the growing point or meristem, such as an imidazalinone or a sulfonylurea. Exemplary genes in this category code for mutant ALS and AHAS enzyme as described, for example, by Lee et al. (1988. *Embryo J.* 7:1241-8) and Miki et al. (1990. *Theoret. Appl. Genet.* 80:449-458).

Resistance genes for glyphosate (resistance conferred by mutant 5-enolpyruvl-3 phosphikimate synthase (EPSP) and aroA genes, respectively) and other phosphono compounds such as glufosinate (phosphinothricin acetyl transferase (PAT), *Streptomyces hygroscopicus* phosphinothricin-acetyl transferase (bar) genes, and pyridinoxy or phenoxy proprionic acids and cyclohexones (ACCase inhibitor-encoding genes) can be used (e.g., see U.S. Pat. No. 4,940,835). Examples of specific EPSPS transformation events conferring glyphosate resistance are described, for example, in U.S. Pat. No. 6,040,497. A DNA molecule encoding a mutant aroA gene can be used (e.g., ATCC accession number 39256 and U.S. Pat. No. 4,769,061). Nucleotide sequences of glutamine synthetase genes which confer tolerance or resistance to herbicides such as L-phosphinothricin are also known (e.g., U.S. Pat. No. 4,975,374). The nucleotide sequence of a PAT gene is known (e.g., U.S. Pat. No. 5,879,903), as is the production of transgenic plants that express chimeric bar genes coding for PAT activity. Exemplary genes conferring resistance to phenoxy proprionic acids and cyclohexones, such as sethoxydim and haloxyfop are the Acc1-S1, Acc1-S2 and Acc1-S3 genes (e.g., see Marshall et al., 1992. *Theor Appl Genet.* 83:435-442). DeGreef et al. (1989. *Bio/Technology* 61-64) describe the production of transgenic plants that express chimeric bar genes coding for phosphinothricin acetyl transferase activity.

Genes conferring resistance to an herbicide that inhibits photosynthesis are also known, such as, a triazine (psbA and gs+ genes) and a benzonitrile (nitrilase gene) (see Przibilla et al., 1991. *Plant Cell.* 3:169-174). Nucleotide sequences for nitrilase genes are disclosed in U.S. Pat. No. 4,810,648, and DNA molecules containing these genes are available under ATCC Accession Nos. 53435, 67441, and 67442. Cloning and expression of DNA coding for a glutathione S-transferase is described by Hayes et al. (1992. *Biochem. J.* 285:173).

U.S. Patent Publication No: 20030135879 describes dicamba monooxygenase (DMO) from *Pseuodmonas maltophilia*, which is involved in the conversion of a herbicidal form of the herbicide dicamba to a non-toxic 3,6-dichlorosalicylic acid and thus can be used for producing plants tolerant to this herbicide.

The metabolism of chlorophenoxyacetic acids, such as, for example 2,4-D herbicide, is well known. Genes or plasmids that contribute to the metabolism of such compounds are described, for example, by Muller et al. (2006. *Appl. Environ. Microbiol.* 72(7):4853-4861), Don and Pemberton (1981. *J Bacteriol* 145(2):681-686), Don et al. (1985. *J Bacteriol* 161(1):85-90) and Evans et al. (1971. *Biochem J* 122(4):543-551).

The enzyme acetohydroxy acid synthase makes plants that express this enzyme tolerant or resistant to multiple types of herbicides.

Other genes that confer tolerance or resistance to herbicides include a gene encoding a chimeric protein of rat cytochrome P4507A1 and yeast NADPH-cytochrome P450 oxidoreductase, genes for glutathione reductase and superoxide dismutase, and genes for various phosphotransferases.

Protoporphyrinogen oxidase (protox) is necessary for the production of chlorophyll, which is necessary for all plant survival. This enzyme serves as the target for a variety of herbicidal compounds. These herbicides also inhibit growth of different species of plants present, causing their total destruction. The development of plants containing altered protox activity that are tolerant or resistant to these herbicides is known.

Disease Resistance

Plant defenses are often activated by specific interaction between the product of a disease resistance gene (R) in the plant and the product of a corresponding avirulence (Avr) gene in the pathogen. A plant, such as 'GA 04570-10E46' or progeny thereof, can be transformed with one or more resistance genes to engineer plants that are resistant to one or more specific pathogens. See, for example Jones et al. (1994. *Science* 266:789) (tomato Cf-9 gene for resistance to *Cladosporium flavum*); Martin et al. (1993. *Science* 262 (5138):1432-1436) (tomato Pto gene for resistance to *Pseudomonas syringae* pv.); and Mindrinos et al. (1994. *Cell* 78:1089-1099) (*Arabidopsis* RSP2 gene for resistance to *Pseudomonas syringae*).

In one example the gene provides resistance or tolerance to a disease, such as a fungal, viral, parasitic, and/or bacterial disease.

A viral-invasive protein or a complex toxin derived therefrom can also be used for viral disease resistance. For example, the accumulation of viral coat proteins in transformed plant cells imparts resistance to viral infection and/or disease development effected by the virus from which the coat protein gene is derived, as well as by related viruses. See Beachy et al. (1990. *Annu Rev Phytopathol* 28:451-474). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

A virus-specific antibody can also be used. See, for example, Tavladoraki et al. (1993. *Nature* 366:469-472), which shows that transgenic plants expressing recombinant antibody genes are protected from virus attack.

Logemann et al. (1992. *Bio/Technology* 10:305-308) disclose transgenic plants expressing a barley ribosome-inactivating gene have an increased resistance to fungal disease.

A developmental-arrestive protein produced in nature can be used. For example, it has been shown that transgenic plants expressing the barley ribosome-inactivating gene have an increased resistance to fungal disease. Thus, fungal endo-α-1,4-D-polygalacturonases facilitate fungal colonization and plant nutrient release by solubilizing plant cell wall homo-.alpha.-1,4-D-galacturonase. Thus a bean endopolygalacturonase-inhibiting protein can be used.

A gene conferring resistance to diseases such as wheat rusts, *Septoria tritici*, *Septoria nodorum*, powdery mildew, *Helminthosporium* diseases, smuts, bunts, *Fusarium* diseases, bacterial diseases, and viral diseases, can be used.

Antifungal genes and genes conferring resistance to nematodes can be used. Genes expressing proteins with antifungal action include those that prevent *Fusarium* head blight, include but are not limited to those encoding endochitinases, exochitinases, glucanases, thionins, thaumatin-like proteins, osmotins, ribosome-inactivating proteins, flavonoids and lactoferricin. During infection with *Fusarium graminearum*, deoxynivalenol is produced, and there is evidence that production of deoxynivalenol increases the virulence of the disease. Thus, genes with properties for detoxification of deoxynivalenol have been engineered for use in wheat. A synthetic peptide that competes with deoxynivalenol has been identified. Changing the ribosomes of the host so that they have reduced affinity for deoxynivalenol has also been used to reduce the virulence of *Fusarium graminearum*. Genes used to help reduce *Fusarium* head blight include but are not limited to Tri101 (*Fusarium*), PDR5 (yeast), tlp-1(oat), tlp-2(oat), leaf tlp-1 (wheat), tip (rice), tlp-4 (oat), endochitinase, exochitinase, glucanase (*Fusarium*), permatin (oat), seed hordothionin (barley), alpha-thionin (wheat), acid glucanase (alfalfa), chitinase (barley and rice), class beta II-1,3-glucanase (barley), PR5/tlp (*Arabidopsis*), zeamatin (maize), type 1 RIP (barley), NPR1 (*Arabidopsis*), lactoferrin (mammal), oxalyl-CoA-decarboxylase (bacterium), IAP (baculovirus), ced-9 (*C. elegans*), and glucanase (rice and barley).

A molecule that stimulates signal transduction can be used, such as calmodulin, such as one from mung bean or maize. A hydrophobic moment peptide can be used, such as peptide derivatives of Tachyplesin, which inhibit fungal plant pathogens, or synthetic antimicrobial peptides that confer disease resistance. A membrane permease, a channel former, or a channel blocker can be used. For example, heterologous expression of a cecropin-β lytic peptide analog can render transgenic plants resistant to *Pseudomonas solanacearum*. Genes involved in the Systemic Acquired Resistance (SAR) response and/or the pathogenesis-related genes can be used. Detoxification genes, such as for fumonisin, beauvericin, moniliformin and zearalenone and their structurally related derivatives can be used. Cystatin and cysteine proteinase inhibitors can be used. Defensin genes can be used.

Insect & Pest Resistance

In one example the gene provides resistance or tolerance to a pest, such as a nematode.

One example of an insect resistance gene includes a *Bacillus thuringiensis* (Bt) protein, a derivative thereof or a synthetic polypeptide modeled thereon (e.g., see Geiser et al., 1986. *Gene* 48:109, discloses a Bt Aendotoxin gene). Moreover, DNA molecules encoding Δ-endotoxin genes can be purchased from the ATCC (Manassas, Va.), for example under ATCC Accession Nos. 40098, 67136, 31995 and 31998.

Another example is a lectin. See, for example, Van Damme et al. (1994. *Plant Mol Biol* 24(5):825-830), which discloses several *Clivia miniata* mannose-binding lectin genes. A vitamin-binding protein can also be used, such as avidin. See WIPO Publication No. WO 1994/000992, which teaches the use of avidin and avidin homologues as larvicides against insect pests.

In one example, the gene that provides resistance or tolerance to a pest is a vitamin-binding protein such as avidin or avidin homologues.

In one example the insect resistance gene is an enzyme inhibitor, for example, a protease, proteinase inhibitor, or an α-amylase inhibitor. See, for example, Abe et al. (1987. *J. Biol. Chem.* 262:16793-7; discloses a rice cysteine proteinase inhibitor), Genbank Accession Nos. Z99173.1 and DQ009797.1 which disclose proteinase inhibitor coding sequences, and Sumitani et al. (1993. *Plant Mol. Biol.* 21:985; discloses *Streptomyces nitrosporeus* α-amylase inhibitor). An insect-specific hormone or pheromone can also be used. See, for example, Hammock et al. (1990. *Nature* 344:458-461; discloses juvenile hormone esterase, an inactivator of juvenile hormone).

An insect-specific hormone or pheromone such as an ecdysteroid and juvenile hormone, a variant thereof, a mimetic based thereon, or an antagonist or agonist thereof, can be used. For example, the baculovirus expression of cloned juvenile hormone esterase, an inactivator of juvenile hormone, can be used.

An insect-specific peptide or neuropeptide which, upon expression, disrupts the physiology of the affected pest can be used. For example, expression cloning yields DNA coding for insect diuretic hormone receptor and an allostatin can be identified in *Diploptera puntata*. Genes encoding insect-specific, paralytic neurotoxins can be used.

An insect-specific venom produced in nature by a snake, a wasp, etc. can be used. For example, heterologous expression of a gene coding for a scorpion insectotoxic peptide, can be used An enzyme responsible for a hyper-accumulation of a monoterpene, a sesquiterpene, a steroid, a hydroxamic acid, a phenylpropanoid derivative or another non-protein molecule with insecticidal activity, can be used.

An enzyme involved in the modification, including the post-translational modification, of a biologically active molecule can be used. Examples of such enzymes include, but are not limited to, a glycolytic enzyme, a proteolytic enzyme, a lipolytic enzyme, a nuclease, a cyclase, a callase, a transaminase, an esterase, a hydrolase, a phosphatase, a kinase, a phosphorylase, a polymerase, an elastase, a chitinase and a glucanase, whether natural or synthetic. DNA molecules which contain chitinase-encoding sequences can be obtained, for example, from the ATCC under Accession Nos. 39637 and 67152. The nucleotide sequences of a cDNA encoding tobacco hookworm chitinase and parsley ubi4-2 polyubiquitin gene are known.

Still other examples include an insect-specific antibody or an immunotoxin derived therefrom and a developmental-arrestive protein. Thus, an antibody targeted to a critical metabolic function in the insect gut would inactivate an affected enzyme, killing the insect. For example, enzymatic inactivation in transgenic tobacco via production of single-chain antibody fragments was shown by Taylor et al. (1994. Seventh Intl. Symposium on Molecular Plant-Microbe Interactions (Edinburgh Scotland), Abstract #497).

A gene, for example, the H9, H10 and H21 genes, conferring resistance to a pest, such as Hessian fly, stem soft fly, cereal leaf beetle, and/or green bug, can be used.

Male Sterility

There are several methods of conferring genetic male sterility available, such as multiple mutant genes at separate locations within the genome that confer male sterility. In addition to these methods, a system of nuclear male sterility that includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on", resulting in the male fertility gene not being transcribed, is known. Fertility is restored by inducing, or turning "on", the promoter, which in turn allows the gene that confers male fertility to be transcribed. In one example, a herbicide-inducible male sterility systems is used (e.g., see U.S. Pat. No. 6,762,344).

In one example, a deacetylase gene under the control of a tapetum-specific promoter is introduced into 'GA 04570-10E46' and/or its progeny and the chemical N—Ac-PPT applied to the transgenic plants.

In one example, a stamen-specific promoter is introduced into 'GA 04570-10E46' and/or its progeny.

In one example, the barnase and the barstar genes are introduced into 'GA 04570-10E46' and/or its progeny.

Where use of male-sterility systems is desired, it can be beneficial to also utilize one or more male-fertility restorer genes. For example, where cytoplasmic male sterility (CMS) is used, hybrid seed production involves three inbred lines: (1) a cytoplasmically male-sterile line having a CMS cytoplasm; (2) a fertile inbred with normal cytoplasm, which is isogenic with the CMS line for nuclear genes ("maintainer line"); and (3) a distinct, fertile inbred with normal cytoplasm, carrying a fertility restoring gene ("restorer" line). The CMS line is propagated by pollination with the maintainer line, with all of the progeny being male sterile, as the CMS cytoplasm is derived from the female parent. These male sterile plants can then be efficiently employed as the female parent in hybrid crosses with the restorer line, without the need for physical emasculation of the male reproductive parts of the female parent. Thus, the disclosure provides plants of the new wheat variety 'GA 04570-10E46' comprising a genetic locus capable of restoring male fertility in an otherwise male-sterile plant. Examples of male-sterility genes and corresponding restorers which can be employed are well known (see, e.g., U.S. Pat. No. 5,530,191 and U.S. Pat. No. 5,684,242).

Modified Fatty Acid, Phytate and Carbohydrate Metabolism and Others

Genes conferring modified fatty acid metabolism can be introduced into 'GA 04570-10E46' and its progeny, such as an antisense gene of stearyl-ACP desaturase to increase stearic acid content of the plant.

Genes conferring modified (e.g., decreased) phytate content can be introduced into 'GA 04570-10E46' and its progeny. For example decreased phytate content can be accomplished by introduction of a phytase-encoding gene that enhances breakdown of phytate, adding more free phosphate to the transformed plant; or by up-regulation of a gene that reduces phytate content. In one example, an *Aspergillus niger* phytase nucleic acid molecule is used (e.g., see Van Hartingsveldt et al., 1993. *Gene* 127:87-94).

Genes conferring modified carbohydrate composition can be introduced into 'GA 04570-10E46' and its progeny. For example, plants can be transformed with a gene coding for an enzyme that alters the branching pattern of starch, or, a gene altering thioredoxin such as NTR and/or TRX and/or a gamma zein knock out or mutant such as cs27 or TUSC27 or en27. For example, a nucleic acid molecule from a *Streptococcus mutans* fructosyltransferase gene (e.g., see Shiroza et al., 1988. *J Bacteriol* 170(2):810-816), *Bacillus subtilis* levansucrase gene (e.g., see Steinmetz et al., 1985. *Mol Gen Genet*. 200:220-228), *Bacillus lichenifonnis* α-amylase gene (e.g., see Pen et al., 1992. *BioTechnology* 10:292) tomato invertase genes (e.g., see Elliot et al., 1993. *Plant Mol. Biol* 21:515) are known and can be used. Transgenic plants can be produced that express *Bacillus licheniformis* alpha-amylase, that site-direct mutagenesis of barley alpha-amylase gene (e.g., see Sergaard et al., 1993. *J. Biol. Chem*. 268:22480)), or confer maize endosperm starch branching enzyme II (e.g., see Fisher et al., 1993. *Plant Physiol* 102:1045) or improved digestibility and/or starch extraction through modification of UDP-D-xylose 4-epimerase. Methods of producing high oil seed by modification of starch levels (AGP) are also known. The fatty acid modification genes mentioned above may also be used to affect starch content and/or composition through the interrelationship of the starch and oil pathways. The Z10 gene encoding a 10 kD zein storage protein from maize can also be used to alter the quantities of 10 kD zein in the cells relative to other components (Kirihara et al., 1988. *Mol Gen Genet*. 211:477-484).

Genes conferring elevated oleic acid can be introduced into 'GA 04570-10E46' and its progeny. For example, this can be achieved by a FAD-2 gene modification and/or decreased linolenic acid via FAD-3 gene modification.

Genes conferring modified conjugated linolenic or linoleic acid content, or LEC1, AGP, Dek1, Superal1, mi1ps, can be introduced into 'GA 04570-10E46' and its progeny. For example, such can be achieved by expression of various Ipa genes such as Ipa1, Ipa3, hpt or hggt.

Genes conferring modified antioxidant content or composition, such as alteration of tocopherol or tocotrienols, can be introduced into 'GA 04570-10E46' and its progeny. For example, this can be achieved by manipulation of antioxidant levels through alteration of a phytl prenyl transferase (ppt), or by alteration of a homogentisate geranyl transferase (hggt).

Genes conferring modified high-molecular weight gluten subunits (HMS-GS) content can be introduced into 'GA 04570-10E46' and its progeny. For example, this can be achieved by using nucleic acid molecules that encode a HMS-GS. For example, genomic clones can be transformed wheat with genes that encode a modified HMW-GS.

Genes conferring increased protein metabolism, zinc and iron content can be introduced into 'GA 04570-10E46' and its progeny. For example, this can be achieved by regulating the NAC gene, increasing protein metabolism by regulating the Gpc-B1 gene, or regulating glutenin and gliadin genes.

Genes conferring altered essential seed amino acids can be introduced into 'GA 04570-10E46' and its progeny. For example, this can be achieved by increasing accumulation of essential amino acids in seeds, binary methods of increasing accumulation of essential amino acids in seeds, alteration of amino acid compositions in seeds, methods for altering amino acid content of proteins, alteration of amino acid compositions in seeds, and proteins with enhanced levels of essential amino acids. Other examples may include high methionine, high threonine, plant amino acid biosynthetic enzymes, increased lysine and threonine, plant tryptophan synthase beta subunit, methionine metabolic enzymes, high sulfur, increased methionine, plant amino acid biosynthetic enzymes, engineered seed protein having higher percentage of essential amino acids, increased lysine, increasing sulfur amino acid content, synthetic storage proteins with defined structure containing programmable levels of essential amino acids for improvement of the nutritional value of plants, increased threonine, increased lysine, Ces A: cellulose synthase, hemicellulose, UDPGdH, and RGP.

Genes can be introduced into 'GA 04570-10E46' and its progeny that permit site-specific recombination. For example, this can be achieved by introduction of FRT sites and/or Lox sites into a wheat plant. FRT sites can be used in the FLP/FRT system. Lox sites can be used in the Cre/Loxp system. Other exemplary systems that may be used include the Gin recombinase of phage Mu, the Pin recombinase of *E. coli*, and the R/RS system of the pSR1 plasmid.

Genes that Affect Abiotic Stress Resistance

Genes that affect abiotic stress resistance (including but not limited to flowering, ear and seed development, enhancement of nitrogen utilization efficiency, altered nitrogen responsiveness, drought resistance or tolerance, cold resistance or tolerance, heat resistance or tolerance, low or high soil pH level resistance or tolerance, and salt resistance or tolerance) and increased yield under stress can be introduced into 'GA 04570-10E46' and its progeny. In some examples, such abiotic stress tolerance can increase yield.

For example, water use efficiency can be altered through alteration of malate. In addition, various genes, including CBF genes and transcription factors can be effective in mitigating the negative effects of freezing, high salinity, and drought on plants, as well as conferring other positive effects on plant phenotype. Abscisic acid can be altered in plants, resulting in improved plant phenotype, such as increased yield and/or increased tolerance to abiotic stress. Cytokinin expression can be modified resulting in plants with increased stress tolerance, such as drought tolerance, and/or increased yield. Nitrogen utilization can be enhanced and/or nitrogen responsiveness can be altered. Ethylene can be altered. Plant transcription factors or transcriptional regulators of abiotic stress can also be altered.

Improved tolerance to water stress from drought or high salt water condition can be conferred to 'GA 04570-10E46' and its progeny. The HVA1 protein belongs to the group 3 LEA proteins that include other members such as wheat pMA2005, cotton D-7, carrot Dc3, and rape pLEA76. These proteins are characterized by 11-mer tandem repeats of amino acid domains which may form a probable amphophilic alpha-helical structure that presents a hydrophilic surface with a hydrophobic stripe. The barley HVA1 gene and the wheat pMA2005 gene are highly similar at both the nucleotide level and predicted amino acid level. These two monocot genes are closely related to the cotton D-7 gene and carrot Dc3 gene with which they share a similar structural gene organization. There is, therefore, a correlation between LEA gene expression or LEA protein accumulation with stress tolerance in a number of plants. For example, in severely dehydrated wheat seedlings, the accumulation of high levels of group 3 LEA proteins was correlated with tissue dehydration tolerance. Studies on several Indica varieties of rice showed that the levels of group 2 LEA proteins (also known as dehydrins) and group 3 LEA proteins in roots were significantly higher in salt-tolerant varieties compared with sensitive varieties. The barley HVA1 gene was transformed into wheat. Transformed wheat plants showed increased tolerance to water stress.

Improved water stress tolerance can be conferred to wheat 'GA 04570-10E46' and its progeny through increased mannitol levels via the bacterial mannitol-1-phosphate dehydrogenase gene.

Other genes and transcription factors that affect plant growth and agronomic traits such as yield, flowering, plant growth and/or plant structure, can be introduced or introgressed into plants.

Other exemplary useful genes and traits for transgenic modification of the 'GA 04570-10E46' variety are disclosed in, for example, U.S. Pat. Nos. 7,687,686, 7,649,127 and 7,645,923.

Tissue Cultures and In Vitro Regeneration of Wheat Plants

Tissue cultures of the new wheat cultivar 'GA 04570-10E46' are provided. A tissue culture includes isolated cells of the same or a different type or a collection of such cells organized into parts of a plant. Exemplary types of tissue cultures include protoplasts, calli and plant cells that are intact in plants or parts of plants, such as embryos, pollen, flowers, leaves, roots, root tips, anthers, meristematic cells, pistil, seed, pod, petiole, stein, ovule, cotyledon, hypocotyl, shoot or stem, and the like. In a particular example, the tissue culture includes embryos, protoplasts, meristematic cells, pollen, leaves or anthers of the new wheat variety 'GA 04570-10E46'. Also provided are wheat plants regenerated from such tissue cultures, wherein the wheat plant expresses the physiological and morphological characteristics of the wheat variety 'GA 04570-10E46'.

Wheat seeds can be regenerated using shoot morphogenesis or somatic embryogenesis. Shoot morphogenesis is the process of shoot meristem organization and development. Shoots grow out from a source tissue and are excised and rooted to obtain an intact plant. During somatic embryogenesis, an embryo (similar to the zygotic embryo), containing both shoot and root axes, is formed from somatic plant tissue. An intact plant rather than a rooted shoot results from the germination of the somatic embryo.

Shoot morphogenesis and somatic embryogenesis are different processes and the specific route of regeneration is primarily dependent on the explant source and media used for tissue culture manipulations. While the systems are different, both systems show variety-specific responses where some lines are more responsive to tissue culture manipulations than others. A line that is highly responsive in shoot morphogenesis may not generate many somatic embryos, while lines that produce large numbers of embryos during an "induction" step may not give rise to rapidly-growing proliferative cultures. In addition to line-specific responses, proliferative cultures can be observed with both shoot morphogenesis and somatic embryogenesis. Proliferation allows a single, transformed cell to multiply to the point that it can contribute to germ-line tissue.

Embryogenic cultures can also be used for regeneration, including regeneration of transgenic plants.

Example 1

Breeding History of 'GA 04570-10E46'

'GA 04570-10E46', winter wheat (*Triticum aestivum* L.), was developed and released in 2013. 'GA 04570-10E46' was derived from the cross of GA00400G1/3/Pioneer 2684/3*AGS 2000/I AGS 2000/GA 84202. GA 00400 is a backcross derived line of 'AGS 2000' which was used due to its resistance to wheat soil-borne mosaic virus. 'GA 84202' was used due to its good leaf and stripe rust resistance (Lr37Yr17). 'PIO 2684' was used as a parent due to its powdery mildew resistance. The final cross of 'GA 04570-10E46' was made in the fall of 2004. The F1 plants were grown in the greenhouse in Griffin, Ga. The population was advanced from the F2 through F5 generations in the field using the modified pedigree method of breeding with individual spikes selected for resistance to leaf rust (caused by *Puccinia recondita* (Roberge ex Desmaz), stripe rust (caused by *Puccinia striiformis* Westend), powdery mildew (caused by *Erysiphe graminis* DC. f. sp. *tritici* Em. Marchal), and *septoria nodorum* blotch (caused by *Stagonospora nodorum* (Berk) Castellani & E. G. Germano). Spikes were harvested, threshed individually and planted in single 1 meter headrows and were advanced to the next generation during the F2:3-, F3:4-, and F4:5-derived lines at Plains, Ga. 'GA 04570-

'10E46' is the F5:derived head row selected and advanced to Breeder Seed which was produced in the F10 generation.

'GA 04570-10E46' was evaluated as 'GA 04570-10E46' for agronomic performance in elite yield nurseries in 2010 at GA, AL, and FL and in multi-locations (GAWN) in 2011 at GA, FL, AR, and VA; GA state trials at five locations from 2011 to 2013, and in the Uniform Southern Soft Red Winter Wheat Nursery in 2012.

Four increase strips of 'GA 04570-10E46' were planted in 2012 in Plains, Ga. from a small increase plot which originated from remnant seed of a headrow in F6 generation. The two middle strips were rogued thoroughly for aberrant types to create breeder seed. Seeds from the increase strips were planted in a 12 acre field in 2013 in Plains, Ga. and rogued to remove variants. 'GA 04570-10E46' has been observed for 3 generations of reproduction and during seed increase period and is stable and uniform. The variants observed included up to 0.01% taller plants, 0.01% plants having apically awnletted heads, 0.05% green, 0.01% late plants and 0.01% early plants.

This Breeder seed of was provided 'GA 04570-10E46' to the Georgia Seed Development Commission and will be the source of future seed multiplications. Breeder seed of 'GA 04570-10E46' will be maintained by the Georgia Agricultural Experiment Station, University of Georgia-Griffin Campus, Griffin, Ga. 30223-1797.

Example 2

Description of 'GA 04570-10E46'

'GA 04570-10E46' is a high grain yielding, medium maturing, excellent test weight, medium height line (Tables 1, 3, 5, 6, 7, 8, 9, 11, 13). Its maturity is similar to 'AGS 2035' in Georgia. It has good resistance to races of leaf rust and stripe rust in Georgia and the Southeast (Tables 2, 4, 10, 12). It is also resistant to wheat soil-borne mosaic virus (Table 2).

'AGS 2035' and 'Baldwin' are the leading cultivars in Georgia and 'SS 8641' is one the leading cultivars in north Georgia.

'GA 04570-10E46' averaged significantly higher in grain yield in State wide and south Georgia trials as compared to 'AGS 2035' and 'Baldwin' on 3-Yr average (2011-13) (Tables 5 and 6).

'GA 04570-10E46' has good powdery mildew resistance (Tables 4, 10, 12) which is better than 'AGS 2035' and 'Baldwin' but is not as good as 'SS 8641'.

TABLE 1

Average Performance of GA entries and Checks in Elite Nursery at Plains, Calhoun and Griffin, GA and Mississippi (Total 4 locs), 2010.

| Entry | Yield bu/A | Test Wt. lbs/bu | Head Date Julian | Height inches |
|---|---|---|---|---|
| GA 04570-10E46 | 74.1a | 59.3a | 107 | 33 |
| AGS 2035 | 75.6a | 58.9a | 105 | 32 |
| Baldwin | 75.9a | 58.8a | 110 | 34 |
| AGS 2060 | 70.7b | 59.9a | 106 | 32 |

Numbers with same letters are not significantly different at the P = 0.05.

TABLE 2

Average Performance of GA entries and Checks in Elite Nursery at Plains, Calhoun and Griffin, GA and Mississippi (Total 4 locs), 2010.

| Entry | Stripe Rust 0-9 | Soil Borne Virus 0-9 |
|---|---|---|
| GA 04570-10E46 | 0.0a | 0.0a |
| AGS 2035 | 0.7a | 0.0a |
| Baldwin | 0.0a | 0.3a |
| AGS 2060 | 0.0a | 8.0b |
| Highest rating | 7 | 9 |

Scale: 0 resistant and 9 susceptible
Numbers with same letters are not significantly different at the P = 0.05.

TABLE 3

Average Performance of GA entries and Checks in Multi-State* Performance Trials (GAWN) (6 Loc.), 2011.

| Entry | Yield bu/A | Test Wt. lbs/bu | Head Date Julian | Height inches |
|---|---|---|---|---|
| GA 04570-10E46 | 86.6a | 59.0b | 98ab | 37a |
| AGS 2060 | 78.8bc | 61.4a | 97b | 38a |
| SS 8641 | 81.6ab | 58.9b | 99a | 38a |
| USG 3555 | 75.9c | 57.2c | 99a | 30b |

*Florida, Georgia, North Carolina, Louisiana, Virginia, and Arkansas
Numbers with same letters are not significantly different at the P = 0.05.

TABLE 4

Average Agronomic Traits of GA entries and Checks in Multi-State* Performance Trials (GAWN), 2011.

| Entry | Powdery Mildew 0-9 | Leaf Rust 0-9 | Stripe Rust 0-9 |
|---|---|---|---|
| GA 04570-10E46 | 1.3b | 0.4b | 0.2a |
| AGS 2060 | 5.5a | 0.0b | 0.4a |
| SS 8641 | 0.0c | 0.1b | 0.2a |
| USG 3555 | 2.3b | 3.9a | 0.0a |
| Highest Rating | 6.8 | 4.8 | 4.0 |

*Florida, Georgia, North Carolina, Louisiana, Virginia, and Arkansas
Scale: 0 resistant and 9 susceptible
Numbers with same letters are not significantly different at the P = 0.05

TABLE 5

Average Performance of GA entries and Checks in Georgia's State Performance Trials in Georgia, 3-Yr Ave, 2011-13 (15 Yr-Loc).

| Entry | Yield bu/A | Test Wt. lbs/bu | Head Date Julian | Height inches |
|---|---|---|---|---|
| GA 04570-10E46 | 86.2a | 59.7a | 91b | 40a |
| AGS 2035 | 80.6b | 59.0a | 90b | 42a |
| Baldwin | 78.9b | 58.0b | 94a | 43a |
| SS 8641 | 86.2a | 57.9b | 93a | 40a |

Plains, Tifton, Midville, Griffin, and Calhoun
Numbers with same letters are not significantly different at the P = 0.10.

TABLE 6

Average Performance of GA entries and Checks for Grain Yield in Georgia's State Performance Trials in Georgia, 3-Yr Ave 2011-2013 (15 Yr-Loc).

| Entry | South bu/A | North. bu/A | Statewide bu/A |
|---|---|---|---|
| GA 04570-10E46 | 82.5a | 90.0ab | 86.2a |
| AGS2035 | 77.9b | 83.2c | 80.6b |
| Baldwin | 73.3c | 84.5bc | 78.9b |
| SS 8641 | 78.7b | 93.7a | 86.2a |

Plains, Tifton, Midville, Griffin, and Calhoun
Numbers with same letters are not significantly different at the P = 0.10.

TABLE 7

Average Performance of GA entries and Checks for Grain Yield in Georgia's State Performance Trials in Georgia, 2011 (5 Yr-Loc).

| Entry | South bu/A | North. bu/A | Statewide bu/A |
|---|---|---|---|
| GA 04570-10E46 | 79.8ab | 92.4a | 84.8ab |
| AGS2035 | 81.8a | 95.2a | 87.1a |
| Baldwin | 74.6c | 95.7a | 83.0ab |
| SS 8641 | 76.5bc | 87.6a | 80.9b |

Plains, Tifton, Midville, Griffin, and Calhoun
Numbers with same letters are not significantly different at the P = 0.10.

TABLE 8

Average Performance of GA entries and Checks for Grain Yield in Georgia's State Performance Trials in Georgia, 2012 (5 Yr-Loc).

| Entry | South bu/A | North. bu/A | Statewide bu/A |
|---|---|---|---|
| GA 04570-10E46 | 78.5a | 94.5a | 84.9a |
| AGS2035 | 74.6a | 95.8a | 83.1ab |
| Baldwin | 67.0b | 94.3a | 77.9b |
| SS8641 | 71.7ab | 97.2a | 81.9ab |

Plains, Tifton, Midville, Griffin, and Calhoun
Numbers with same letters are not significantly different at the P = 0.10.

TABLE 9

Average Performance of GA entries and Checks for Grain Yield in Georgia's State Performance Trials in Georgia, 2013 (5 Yr-Loc).

| Entry | South bu/A | North. bu/A | Statewide bu/A |
|---|---|---|---|
| GA 04570-10E46 | 89.4a | 111.9b | 100.7a |
| AGS2035 | 77.2b | 87.8d | 82.5b |
| Baldwin | 78.2b | 97.7c | 87.9b |
| SS8641 | 88.0a | 129.3a | 108.7a |

Plains, Tifton, Midville, and Griffin
Numbers with same letters are not significantly different at the P = 0.10.

TABLE 10

Average Performance of GA entries and Checks in Georgia's State Performance Trials during 2011-2013.

| Entry | Leaf Rust+ 0-9* | Powdery Mildew++ 0-9 | Stripe Rust++ 0-9 |
|---|---|---|---|
| GA 04570-10E46 | 0.0a | 0.5c | 0.0a |
| AGS2035 | 0.0a | 4.5a | 0.0a |
| Baldwin | 0.0a | 3.0b | 0.0a |
| SS 8641 | 0.0a | 0.0c | 0.0a |
| Highest rating | 8.0 | 6.0 | 8.0 |

Scale: 0 resistant and 9 susceptible
+Leaf rust 3-Yr Average
++Powdery Mildew and Stripe rust 2-Yr Average
Numbers with same letters are not significantly different at the P = 0.10.

TABLE 11

Average Performance of GA entries and Checks in Uniform Southern Soft Red Winter Nursery, 2012.

| Entry | Yield bu/A | Test Wt. lbs/bu | Head Date Julian | Height inches | Lodging 0-9 |
|---|---|---|---|---|---|
| GA 04570-10E46 | 66.9a | 59.2a | 94b | 35a | 1.5b |
| AGS 2000 | 59.9b | 57.5b | 94b | 34b | 3.0a |
| PIO 26R61 | 58.3b | 58.9a | 96a | 35b | 1.0b |
| USG 3555 | 66.5a | 56.8b | 97a | 31c | 2.0ab |
| Jamestown | 67.8a | 56.9b | 93b | 31c | 2.5ab |

21 locations in the Southern Region
Numbers with same letters are not significantly different at the P = 0.05.

TABLE 12

Average Agronomic Traits of GA lines and Checks in Uniform Southern Soft Red Winter Nursery, 2012.

| Entry | Leaf Rust 0-9 | Stripe Rust 0-9 | Powdery Mildew 0-9 |
|---|---|---|---|
| GA 04570-10E46 | 0.2c | 1.0c | 1.4b |
| AGS 2000 | 1.5b | 4.1a | 3.8a |
| PIO 26R61 | 1.6b | 2.1b | 2.1b |
| USG 3555 | 4.7a | 1.0c | 1.0b |
| Jamestown | 2.8b | 1.0c | 1.5b |

21 locations in the Southern Region
Scale: 0 resistant and 9 susceptible
Numbers with same letters are not significantly different at the P = 0.05.

TABLE 13

Average Performance (Bu/A) of GA lines and Checks in Uniform Southern Soft Red Winter Nursery, 2012.

| Entry | AL | AR | GR GA | PL GA | NC | MS | TX | VA |
|---|---|---|---|---|---|---|---|---|
| GA 04570-10E46 | 62 | 71 | 87 | 102 | 72 | 44 | 87 | 79 |
| AGS 2000 | 64 | 68 | 59 | 67 | 55 | 45 | 70 | 78 |
| PIO 26R61 | 56 | 58 | 63 | 76 | 76 | 39 | 71 | 74 |
| USG 3555 | 53 | 63 | 71 | 82 | 88 | 42 | 86 | 94 |
| Jamestown | 57 | 60 | 80 | 94 | 80 | 47 | 87 | 92 |

21 locations in the Southern Region

Example 3

'GA 04570-10E46' is Resistant to Hessian Fly

'GA 04570-10E46' has good resistance in the field to current biotypes of Hessian fly in Georgia (Table 14). 'GA 04570-10E46' has better Hessian fly resistance than 'AGS 2035' and 'Baldwin', especially in Plains, Ga.

TABLE 14

Evaluation of lines as % fly infestation in the field to Hessian fly at Plains Griffin and Tifton, GA in 2012 and 2013.

| Entry | 2012 Plains | 2012 Griffin | 2013 Plains | 2013 Griffin | 2013 Tifton |
|---|---|---|---|---|---|
| GA 04570-10E46 | 3a | 0a | 1c | 0b | 0b |
| Baldwin | 17b | 0a | 50b | 10ab | 0b |
| AGS 2035 | 15b | 15b | 37b | 15ab | 5b |
| SS 8641 | 25b | 5a | 7a | 20a | 10b |
| USG 3555 | 80a | 15b | 78a | 20a | 60a |

Numbers with same letters are not significantly different at the P = 0.10.

Example 4

'GA 04570-10E46' Milling and Baking Quality

'GA 04570-10E46' has acceptable milling and baking quality as a soft red winter wheat, as evaluated by the USDA-Soft Wheat Quality Laboratory, Wooster, Ohio (Table 15).

TABLE 15

Evaluation for Soft Wheat Milling and Baking Quality* 2012.

| Entry | Milling Quality Score | Baking Quality Score | Flour Yield % |
|---|---|---|---|
| GA 04570-10E46 | 82A | 67C | 72a |
| AGS 2000 | 77B | 52D | 71a |
| PIO 26R61 | 61C | 51D | 68a |

*Evaluated by USDA ARS Wheat Quality Lab., Wooster, OH

Example 5

Production of 'GA 04570-10E46' Wheat

'GA 04570-10E46' can be grown under normal conditions for growing wheat, and bulk seed for large-scale planting can be obtained by methods known in certified seed production. For example, bulk seed may be produced by planting 'GA 04570-10E46' seeds obtained from ATCC Accession No: PTA-123659, allowing the mature plants to self-produce seed by self-pollination with each other and then collecting the seed. Standard precautions can be taken to prevent cross-pollination from other wheat, such as growing the variety in an isolated plot of sterilized soil, removing adjacent vegetation, etc. The 'GA 04570-10E46' seeds deposited with ATCC are breeder seeds; propagation of plants from these seeds can be performed under standard conditions known to those skilled in the art.

Example 6

Introducing Traits of 'GA 04570-10E46' into Other Wheat Cultivars

The morphological and physiological characteristics of 'GA 04570-10E46', including resistance to many pests that affect wheat (including resistance to leaf rust (e.g., races MCTNB, TDBGG, TBBGJ, TNRJ, MCDS, KFBJ, MLDS, TCRKG, TFBJ, and TCTSB), resistance to stem rust (e.g., stem rust races, QFCSC, QTHJC, RCRSC, RKQQC, TTTTF, SCCSC, and QCCSM), resistance to stripe rust, resistance to soil-borne mosaic virus, resistance to powdery mildew, and resistance to Hessian flies) as well as medium maturing, high yield, excellent test weight, acceptable milling and baking quality characteristics, can be introduced into other wheat varieties (such as other soft red winter wheat cultivars) by conventional breeding techniques. For example, 'GA 04570-10E46' can be grown in pollination proximity to another variety of wheat, allowing cross-pollination to occur between 'GA 04570-10E46' and the other variety, and then harvesting the hybrid seeds. Plants grown from these hybrid seeds can then be tested for the maintenance of the characteristics described herein for 'GA 04570-10E46' (such as one or more of resistance to leaf rust (e.g., races MCTNB, TDBGG, TBBGJ, TNRJ, MCDS, KFBJ, MLDS, TCRKG, TFBJ, and TCTSB), resistance to stem rust (e.g., stem rust races, QFCSC, QTHJC, RCRSC, RKQQC, TTTTF, SCCSC, and QCCSM), resistance to stripe rust, resistance to soil-borne mosaic virus, resistance to powdery mildew, and resistance to Hessian flies, as well as medium maturing, high yield, excellent test weight, and/or acceptable milling and baking quality characteristics), and/or the plants can simply be observed to see if they display the same or similar growth characteristics, seed yield, pest resistance, and milling and baking quality described in the Tables 1-15.

For example, plants grown from these hybrid seeds can be tested for any of the morphological characteristics described herein, such as resistance to one or more of leaf rust (e.g., races MCTNB, TDBGG, TBBGJ, TNRJ, MCDS, KFBJ, MLDS, TCRKG, TFBJ, and TCTSB), stem rust (e.g., stem rust races, QFCSC, QTHJC, RCRSC, RKQQC, TTTTF, SCCSC, and QCCSM), stripe rust, soil-borne mosaic virus, powdery mildew, and Hessian flies. In this way, resistance one or more of leaf rust (e.g., races MCTNB, TDBGG, TBBGJ, TNRJ, MCDS, KFBJ, MLDS, TCRKG, TFBJ, and TCTSB), stem rust (e.g., stem rust races, QFCSC, QTHJC, RCRSC, RKQQC, TTTTF, SCCSC, and QCCSM), stripe rust, soil-borne mosaic virus, powdery mildew, and Hessian flies, alone or in combination with one or more of medium maturing, high yield, excellent test weight, and/or acceptable milling and baking quality characteristics may be combined with other desirable plant characteristics. Thus, the provision of 'GA 04570-10E46' enables the production of progeny plants of 'GA 04570-10E46' having resistance to leaf rust (e.g., races MCTNB, TDBGG, TBBGJ, TNRJ, MCDS, KFBJ, MLDS, TCRKG, TFBJ, and TCTSB), resistance to stem rust (e.g., stem rust races, QFCSC, QTHJC, RCRSC, RKQQC, TTTTF, SCCSC, and QCCSM), resistance to stripe rust, resistance to soil-borne mosaic virus, resistance to powdery mildew, and/or resistance to Hessian flies, and in some examples also one or more of medium maturing, high yield, excellent test weight, and/or acceptable milling and baking quality characteristics. "Progeny plants" of 'GA 04570-10E46' are any plants that are the offspring of a cross between 'GA 04570-10E46' and any other plant or plants. Progeny plants also include successive generations of the offspring, for example those selected for resistance to one or more of leaf rust (e.g., races MCTNB, TDBGG, TBBGJ, TNRJ, MCDS, KFBJ, MLDS, TCRKG, TFBJ, and TCTSB), resistance to stem rust (e.g., stem rust races, QFCSC, QTHJC, RCRSC, RKQQC, TTTTF, SCCSC, and QCCSM), resistance to stripe rust, resistance to soil-borne mosaic virus, resistance to powdery mildew, and/or resistance to Hessian flies, and in some examples resistance to all of these, and in some examples one or more of medium maturing, high yield, excellent test weight, and/or acceptable milling and baking quality characteristics. First-generation progeny plants may retain the resistance to leaf rust (e.g., races MCTNB, TDBGG, TBBGJ, TNRJ, MCDS, KFBJ, MLDS, TCRKG, TFBJ, and TCTSB), resistance to stem rust (e.g., stem rust races, QFCSC, QTHJC, RCRSC, RKQQC, TTTTF, SCCSC, and QCCSM), resistance to stripe rust, resistance to soil-borne mosaic virus, resistance to powdery mildew, and resistance to Hessian flies, as well as medium maturing, high yield, excellent test weight, and/or acceptable milling and baking quality characteristics, of the 'GA 04570-10E46' parent. However, if a first-generation progeny plant does not retain the desired level of resistance to leaf rust (e.g., races MCTNB, TDBGG, TBBGJ, TNRJ, MCDS, KFBJ, MLDS, TCRKG, TFBJ, and TCTSB), resistance to stem rust (e.g., stem rust races, QFCSC, QTHJC, RCRSC, RKQQC, TTTTF, SCCSC, and QCCSM), resistance to stripe rust, resistance to soil-borne mosaic virus, resistance to powdery mildew, and resistance to Hessian flies, as well as medium maturing, high yield, excellent test weight, and/or acceptable milling and baking quality characteristics, observed with 'GA 04570-10E46', subsequent generations of offspring can be recycled for resistance to these pests which have at least the same resistance to these pests as does 'GA 04570-10E46' described herein. In one embodiment, subsequent generations of offspring can have resistance to leaf rust (e.g., races MCTNB, TDBGG, TBBGJ, TNRJ, MCDS, KFBJ, MLDS, TCRKG, TFBJ, and TCTSB), resistance to stem rust (e.g., stem rust races, QFCSC, QTHJC, RCRSC, RKQQC, TTTTF, SCCSC, and QCCSM), resistance to stripe rust, resistance to soil-borne mosaic virus, resistance to powdery mildew, and resistance to Hessian flies, as well as medium maturing, high yield, excellent test weight, and/or acceptable milling and baking quality characteristics, similar to that or even that exceed that of 'GA 04570-10E46'.

In addition, 'GA 04570-10E46' can be used as transformation targets for the production of transgenic wheat. In certain embodiments, the present disclosure contemplates the transformation of cells derived from 'GA 04570-10E46' with at least one transgene. For example, transgenes that can be used, include, but are not limited to, transgenes that confer resistance to one or more of herbicide tolerance, drought tolerance, heat tolerance, low or high soil pH level tolerance, salt tolerance, resistance to an insect, resistance to a bacterial disease, resistance to a viral disease, resistance to a fungal disease, resistance to a nematode, resistance to a pest, male sterility, site-specific recombination; abiotic stress tolerance; modified phosphorus characteristics; modified antioxidant characteristics; modified essential seed amino acid characteristics; modified fatty acid metabolism, and modified carbohydrate metabolism. Examples of such genes and methods of transforming plants are described in U.S. Pat. No. 6,025,545.

Example 7

Production of Double Haploids

The production of double haploids can also be used for the development of plants with a homozygous phenotype in a breeding program. For example, a wheat plant for which wheat cultivar 'GA 04570-10E46'-892 is a parent can be used to produce double haploid plants. Double haploids are produced by the doubling of a set of chromosomes (1 N) from a heterozygous plant to produce a completely homozygous individual. This process omits the generations of selfing needed to obtain a homozygous plant from a heterozygous source.

Haploid induction systems have been developed for various plants to produce haploid tissues, plants and seeds. The haploid induction system can produce haploid plants from any genotype by crossing a selected line (as female) with an inducer line. Methods for obtaining haploid plants are known.

Thus, methods for making a substantially homozygous 'GA 04570-10E46' progeny plant are provided, for example by producing or obtaining a seed from the cross of 'GA 04570-10E46' and another wheat plant and applying double haploid methods to the $F_1$ seed or $F_1$ plant or to any successive filial generation. Such methods may decrease the number of generations required to produce a variety with similar genetics or characteristics to 'GA 04570-10E46'.

In particular, a process of making seed retaining the molecular marker profile of wheat variety 'GA 04570-10E46' can include obtaining or producing $F_1$ seed for which wheat variety 'GA 04570-10E46' is a parent, inducing doubled haploids to create progeny without the occurrence of meiotic segregation, obtaining the molecular marker profile of wheat variety 'GA 04570-10E46', and selecting progeny that retain the molecular marker profile of 'GA 04570-10E46'. Other breeding methods that are commonly used for different traits and crops are known.

Further reproduction of the variety can occur by tissue culture and regeneration. Tissue culture of various tissues of wheat and regeneration of plants therefrom is well known. Thus, provided herein are cells which upon growth and differentiation produce wheat plants having essentially all of the physiological and morphological characteristics of wheat cultivar 'GA 04570-10E46'. Means for preparing and maintaining plant tissue culture are well known in the art. By way of example, a tissue culture comprising organs has been used to produce regenerated plants.

In view of the many possible embodiments to which the principles of the disclosure may be applied, it should be recognized that the illustrated embodiments are only examples of the disclosure and should not be taken as limiting the scope of the invention. Rather, the scope of the disclosure is defined by the following claims. We therefore claim as our invention all that comes within the scope and spirit of these claims.

We claim:

1. A seed of wheat cultivar 'GA 04570-10E46', wherein a representative sample of seed of the cultivar has been deposited under American Type Culture Collection (ATCC) Accession No. PTA-123659.

2. A seed mixture, comprising the seed of claim 1.

3. A wheat plant of wheat cultivar 'GA 04570-10E46', wherein a representative sample of seed of the cultivar has been deposited under ATCC Accession No. PTA-123659.

4. A plant part of the wheat plant of claim 3.

5. The plant part of claim 4, wherein the plant part is pollen, an ovule, a head, an awn, a leaf, an embryo, a cotyledon, a hypocotyl, a meristematic cell, a root, a root tip, a pistil, an anther, a floret, a pericarp, a spike, a stern, a callus, or a cell.

6. A tissue culture produced from protoplasts or cells from the wheat plant of claim 3.

7. The tissue culture of claim 6, wherein the cells or protoplasts are produced from a leaf, stem, protoplast, pollen, ovule, embryo, cotyledon, hypocotyl, meristematic cell, root, root tip, pistil, anther, flower, seed, shoot, stein, pod or petiole.

8. A wheat plant regenerated from the tissue culture of claim 7, wherein the regenerated wheat plant comprises all of the physiological and morphological characteristics of the wheat cultivar 'GA 04570-10E46'.

9. A method of producing wheat seed, comprising:
crossing the wheat plant of claim 3 with itself or a second wheat plant; and
harvesting a resulting wheat seed.

10. A wheat seed produced by the method of claim 9.

11. A wheat plant, or a part thereof, produced by growing the seed of claim 10.

12. The method of claim 9, wherein the second wheat plant is transgenic.

13. An $F_1$ hybrid seed produced by the method of claim 9.

14. A method of producing a plant of wheat cultivar 'GA 04570-10E46' comprising an added desired trait, comprising:
introducing a transgene conferring the desired trait into the plant of claim 3, thereby producing a plant of wheat cultivar 'GA 04570-10E46' comprising the added desired trait.

15. The method of claim 14, wherein the desired trait is one or more of herbicide tolerance, drought tolerance, heat tolerance, low or high soil pH level tolerance, salt tolerance, resistance to an insect, resistance to a bacterial disease, resistance to a viral disease, resistance to a fungal disease, resistance to a nematode, resistance to a pest, male sterility, site-specific recombination; abiotic stress tolerance, modified phosphorus characteristics, modified antioxidant characteristics; modified essential seed amino acid characteristics, decreased phytate, modified fatty acid metabolism, and modified carbohydrate metabolism.

16. The method of claim 15, wherein the modified fatty acid metabolism or modified carbohydrate metabolism is produced by introducing a gene encoding a protein selected from the group consisting of glutenins, gliadins, phytase, fructosyltransferase, levansucrase, a-amylase, invertase and starch branching enzyme, or encoding an antisense of stearyl-ACP desaturase.

17. The method of claim 15, wherein the resistance to an insect or pest is conferred by a transgene encoding a *Bacillus thuringiensis* (Bt) endotoxin.

18. The method of claim 15, wherein the herbicide tolerance comprises tolerance to an herbicide comprising glyphosate, sulfonylurea, imidazolinone, dicamba, glufosinate, phenoxy proprionic acid, L-phosphinothricin, cyclohexone, cyclohexanedione, triazine, benzonitrile, broxynil, chlorophenoxy acetic acid or combinations thereof.

19. A plant produced by the method of claim 14.

20. A method of introducing a desired trait into wheat cultivar 'GA 04570-10E46' comprising:
(a) crossing the wheat plant of claim 3 with a second wheat plant comprising a desired trait to produce $F_1$ progeny plants;
(b) selecting one or more $F_1$ progeny plants that have the desired trait to produce selected $F_1$ progeny plants;
(c) crossing the selected progeny plants with at least a first plant of cultivar 'GA 04570-10E46' to produce backcross progeny plants;
(d) selecting backcross progeny plants that have the desired trait and all of physiological and morphological characteristics of wheat cultivar 'GA 04570-10E46' to produce selected backcross progeny plants; and
(e) repeating steps (c) and (d) one or more times in succession to produce selected second or higher backcross progeny plants that comprise the desired trait and all of the physiological and morphological characteristics of wheat cultivar 'GA 04570-10E46' when grown in the same environmental conditions.

21. The method of claim 20, wherein the desired trait comprises one or more of herbicide tolerance, drought tolerance, heat tolerance, low or high soil pH level tolerance, salt tolerance, resistance to an insect, resistance to a bacterial disease, resistance to a viral disease, resistance to a fungal disease, resistance to a nematode, resistance to a pest, male sterility, site-specific recombination; abiotic stress tolerance, modified phosphorus characteristics, modified antioxidant characteristics; modified essential seed amino acid characteristics, decreased phytate, modified fatty acid metabolism, and modified carbohydrate metabolism.

22. A wheat plant produced by the method of claim 21, wherein the plant has the desired trait and all of the physiological and morphological characteristics of the wheat cultivar 'GA 04570-10E46'.

23. A plant of wheat cultivar 'GA 04570-10E46', further comprising a single locus conversion, wherein a representative sample of seed of the cultivar has been deposited under ATCC Accession No. PTA-123659.

24. The plant of claim 23, wherein the single locus conversion is introduced into the plant by backcrossing or genetic transformation.

25. A wheat plant produced by transforming the wheat plant of claim 3 with a transgene that confers upon the wheat plant a desired trait, wherein the desired trait is one or more of herbicide tolerance, drought tolerance, heat tolerance, low or high soil pH level tolerance, salt tolerance, resistance to an insect, resistance to a bacterial disease, resistance to a viral disease, resistance to a fungal disease, resistance to a nematode, resistance to a pest, male sterility, site-specific recombination; abiotic stress tolerance, modified phosphorus characteristics, modified antioxidant characteristics; modified essential seed amino acid characteristics, decreased phytate, modified fatty acid metabolism, and modified carbohydrate metabolism.

26. A method of producing an inbred wheat plant derived from wheat cultivar 'GA 04570-10E46', comprising:
(a) preparing a progeny plant derived from wheat cultivar 'GA 04570-10E46' by crossing a plant of the wheat cultivar 'GA 04570-10E46' with a wheat plant of a second variety;
(b) crossing the progeny plant with itself or a second plant to produce a seed of a progeny plant of a subsequent generation;
(c) growing a progeny plant of a subsequent generation from said seed and crossing the progeny plant of a subsequent generation with itself or a second plant; and
(d) repeating steps (b) and (c) for an additional 3-10 generations with sufficient inbreeding to produce an inbred wheat plant derived from the wheat cultivar 'GA 04570-10E46', wherein a representative sample of seed of the cultivar has been deposited under ATCC Accession No. PTA-123659.

27. An inbred plant produced by the method of claim 26, wherein the inbred plant has all of the physiological and morphological characteristics of the wheat cultivar 'GA 04570-10E46'.

28. A wheat seed produced by crossing two wheat plants and harvesting the resultant wheat seed, wherein at least one of the two wheat plants is the wheat plant of claim 3.

29. A wheat plant, or a part thereof, produced by growing said seed of claim 28.

30. A method of producing a commodity plant product comprising:
obtaining the wheat plant of claim 3 or a part thereof; and
producing the commodity plant product therefrom.

31. The method of claim 30, wherein the commodity plant product is grain, flour, biofuel, straw, or starch.

32. A product comprising a wheat plant or a part thereof of wheat cultivar 'GA 04570-10E46', wherein the product is grain, flour, a baked good, cereal, pasta, a beverage, livestock feed, biofuel, straw, construction material, bread, cookie, cake, cracker, noodle, or laundry starch, wherein a representative sample of seed of the cultivar has been deposited under ATCC Accession No. PTA-123659.

33. A composition comprising a seed or plant part of wheat cultivar 'GA 04570-10E46' and a cultivation medium, wherein a representative sample of seed of the cultivar has been deposited under ATCC Accession No. PTA-123659.

34. The composition of claim 33, wherein the cultivation medium is soil or a synthetic medium.

* * * * *